(12) United States Patent
Navarijo

(10) Patent No.: US 11,590,304 B2
(45) Date of Patent: Feb. 28, 2023

(54) VOLUME CONTROL DEVICE FOR MANUALLY OPERATED RESUSCITATOR AND VENTILATION APPARATUS AND METHOD OF USE

(71) Applicant: THE BOARD OF REGENTS OF THE UNIVERSITY OF TEXAS SYSTEM, Austin, TX (US)

(72) Inventor: Craig Navarijo, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 334 days.

(21) Appl. No.: 16/325,869

(22) PCT Filed: Aug. 15, 2017

(86) PCT No.: PCT/US2017/046982
§ 371 (c)(1),
(2) Date: Feb. 15, 2019

(87) PCT Pub. No.: WO2018/035137
PCT Pub. Date: Feb. 22, 2018

(65) Prior Publication Data
US 2019/0209794 A1    Jul. 11, 2019

Related U.S. Application Data

(60) Provisional application No. 62/417,476, filed on Nov. 4, 2016, provisional application No. 62/375,178, filed on Aug. 15, 2016.

(51) Int. Cl.
*A61M 16/00* (2006.01)
*A61M 16/20* (2006.01)

(52) U.S. Cl.
CPC .... *A61M 16/0084* (2014.02); *A61M 16/0078* (2013.01); *A61M 16/208* (2013.01);
(Continued)

(58) Field of Classification Search
CPC ............... A47C 27/081; A61B 5/0002; A61M 16/0057; A61M 16/0078; A61M 16/0084;
(Continued)

(56) References Cited

U.S. PATENT DOCUMENTS 3,046,978 A    7/1962  Lea
4,898,166 A *  2/1990  Rose ................. A61M 16/0078
                                                128/205.13

(Continued)

FOREIGN PATENT DOCUMENTS

TW    201136624    11/2011

OTHER PUBLICATIONS

International Preliminary Report on Patentability issued in Application No. PCT/US2017/046982, dated Feb. 19, 2019.
(Continued)

*Primary Examiner* — Annette Dixon
(74) *Attorney, Agent, or Firm* — Norton Rose Fulbright US LLP

(57) ABSTRACT

A resuscitation bag (bag valve mask resuscitator or BVM or BVMR) or other similar ventilation device (for example: anesthesia bag) includes a structure that allows a selectable, and repeatable volume be delivered to patients. The reservoir of the BVMR is formed from elastic, gastight material in the form of an elongated hollow body, with an essentially circular cross section. A range of motion control (ROMC) structure controls, or selectively limits the range of motion or collapse of the elastic bag to limit or control the volume expelled from the bag to the patient.

11 Claims, 28 Drawing Sheets

(52) U.S. Cl.
CPC ............ *A61M 2205/583* (2013.01); *A61M 2205/586* (2013.01); *A61M 2207/00* (2013.01)

(58) Field of Classification Search
CPC .......... A61M 16/0816; A61M 16/1005; A61M 16/12; A61M 2209/088; A62B 18/006; F04B 43/084; G09B 23/28; G09B 23/288; G16H 40/63; Y10S 2/03
See application file for complete search history.

(56) References Cited

U.S. PATENT DOCUMENTS

| | | | |
|---|---|---|---|
| 5,345,929 A | | 9/1994 | Jansson et al. |
| 5,520,173 A | | 5/1996 | Kuhn |
| 5,645,056 A | * | 7/1997 | Pomeroy ............ A47C 27/081 |
| | | | 128/205.13 |
| 5,711,295 A | * | 1/1998 | Harris, II ......... A61M 16/0057 |
| | | | 128/202.28 |
| 7,658,188 B2 | | 2/2010 | Halpern et al. |
| 2008/0087285 A1 | * | 4/2008 | Kuo ................... A61M 16/0084 |
| | | | 128/205.13 |
| 2008/0210238 A1 | * | 9/2008 | Huddlestone ..... A61M 16/0078 |
| | | | 128/205.14 |
| 2010/0263670 A1 | | 10/2010 | Pearce |
| 2010/0285439 A1 | * | 11/2010 | Mestad ................. G09B 23/28 |
| | | | 434/272 |
| 2011/0120472 A1 | | 5/2011 | Lee et al. |
| 2013/0180527 A1 | | 7/2013 | Kim et al. |
| 2014/0000613 A1 | | 1/2014 | Hines |
| 2017/0015738 A1 | | 1/2017 | Pedersen et al. |

OTHER PUBLICATIONS

International Search Report and Written Opinion issued in Application No. PCT/US2017/046982, dated Jan. 4, 2018.

* cited by examiner

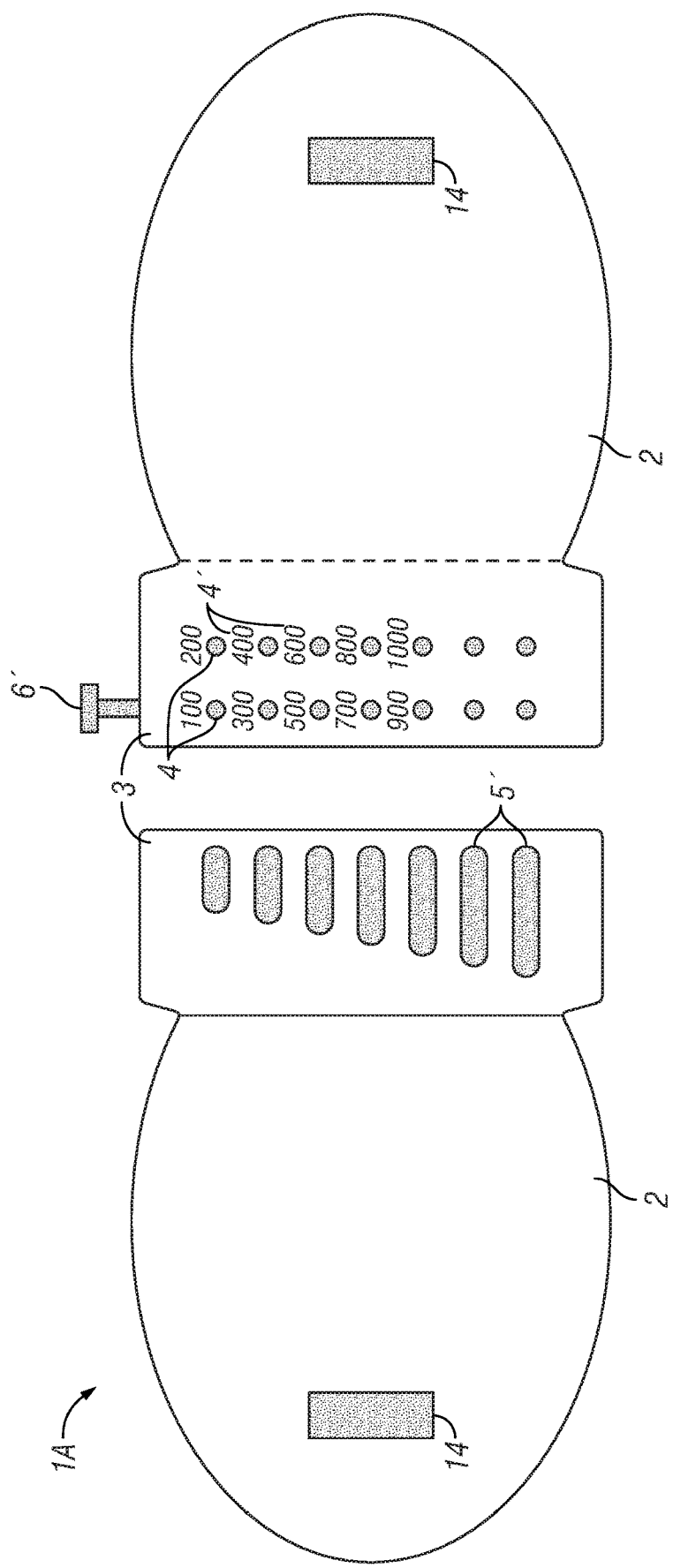

VOLUME CONTROL DEVICE FOR MANUALLY OPERATED RESUSCITATOR AND VENTILATION APPARATUS AND METHOD OF USE

CROSS-REFERENCE TO RELATED APPLICATIONS

This application is a national phase application under 35 U.S.C. § 371 of International Application No. PCT/US2017/046982, filed Aug. 15, 2017 which claims priority to U.S. Provisional Application No. 62/375,178, filed Aug. 15, 2016, and U.S. Provisional Application No. 62/417,476, filed Nov. 4, 2016. The entire contents of each are specifically incorporated by reference herein in their entirety without disclaimer.

BACKGROUND

1. Field of the Invention

The present disclosure relates to devices and methods for controlling the volume of air delivered by a resuscitation bag (bag valve mask resuscitator or BVM or BVMR) or other similar ventilation device (for example: anesthesia bag).

2. Description of Related Art

Generally, bag valve mask resuscitators (BVMR or BVM) are devices that are generally used in emergency situations where a patient has stopped breathing or is having marked difficulty breathing. BVMRs are predominantly stocked and used in ambulances, hospitals, emergency centers, intensive care units, and operating rooms. It is estimated that every person in developed countries will be ventilated with a BVMR at least once in their life.

Volume requirements vary due to anatomical differences (size and weight, space within the thoracic cavity, etc.). Recent science suggests that during cardiac arrest, volume and pressure needs will vary. A patient's needs change during the progression of a cardiac arrest, or other respiratory emergencies (i.e., COPD, Asthma attack), as the patient's lung compliance and cellular respiration needs change. Lung compliance has been proven to diminish over time during cardiac arrest, with forced ventilation becoming more necessary as the event persists (necessary for gas exchange at the alveoli).

Guidelines for cardiopulmonary resuscitation recommend that a patient be ventilated with volumes sufficient to just cause rise and fall of the chest of the patient. In adults, this volume is estimated to be 6-8 mls per kg. This calculation results in every person having different recommended volumes. For example, a person weighing 200 lbs. or 90 kg should receive an estimated 540-720 mls of air or air and oxygen mixture per breath. However, since adult BVMRs usually have volume and ventilation capacities of about 1500 to 1200 cc (BVMs produced in Korea usually have ventilation capability of about 1700 cc), it is difficult to keep the volume delivered during ventilation correct or appropriate using BVMs. The user of the BVMR must decide when to stop squeezing in order for volume to stop being ejected from the BVMR and into the patient's lungs. Some present day BVMRs have "stair stepped" designs that reduce volumes in specific regions of the BVMR to represent complete, maximum, adult, pediatric, or infant standard volumes, but do not allow for a volume less than the maximum to be selected. If the user squeezes that region of the designated BVMR a complete volume of that region of the bag is expelled. If the user wishes to deliver less than the complete amount as designated, he or she must "guesstimate" when to stop compressing the BVMR. None allow the user to calculate the patient's recommended volume, and deliver it with repeatable, relative accuracy. Only the user's ability to gauge the volume being expelled controls the volume administered to a patient in present designs.

Present BVMRs have no way of identifying or controlling the volume that is expelled or administered to a patient. It is completely up to the provider to squeeze the reservoir adequately and to stop squeezing at the appropriate point. Pediatric and infant patients have lower volume requirements due to size differences. Present day BVMRs are constructed in various sizes for specific groups of patients, for example: infant, pediatric, and adult. Each unit has a different capacity, and it is up to the user to determine how much to squeeze the bag to generate appropriate rise and fall of the chest of the patient (a secondary benefit of a universal BVMR may be the reduction of inventory worldwide as the different sizes of BVMRs would no longer be necessary). Present day BVMRs (of all sizes) have no indicators of any kind that gauge or give the user any idea of the actual volume they are delivering to the patient. Often, the user administers either inadequate volume to properly ventilate a patient because they stop squeezing the bag too soon or they can deliver up to the entire volume of the BVMR because there is no built in stop or control mechanism. This can result in delivery of several times the appropriate volume for a patient. The provider can continue to squeeze the bag excessively, thereby causing excess volume to exit the reservoir and to enter the patient.

The volume administered to a patient is largely controlled according to the skill, competence, and/or the ability of the operator of the BVMR. Despite training, there exists a significant frequency of over ventilation of patients by providers. In recent years, much study has been given to the development of intra thoracic pressure due to over inflation of the patient's lungs during use of the BVMR. This causes the lungs of the patient to expand as they fill with air, and to fill the space within the chest cavity. This enlarging of the lungs applies pressure to the heart, and the major vessels in the chest which results in reduced circulation and poor or negative outcomes for patients. There is a need to control with specificity the volume delivered to a patient by the BVMR.

U.S. Pat. No. 5,520,173 teaches a construction of a BVMR that allows for different volumes to be delivered in a generic sense. By "stair stepping" regions of the BVMR to represent the standard volumes of the various sizes of BVMRs (adult, pediatric, infant), the BVMR allows the user to choose a region of the bag, that with complete squeeze causes the user to deliver up to the recommended limitation for tidal volume by population. If less than the upper most recommended volume is necessary due to anatomical difference, the user must gauge on tactile feel alone when to stop compressing the BVMR. U.S. Pat. No. 7,658,188 teaches a BVMR design that allows the user to select or adjust the size of the reservoir with a "skeleton" of a mechanism within the BVMR. This device appears slow to operate and impractical in emergency situations as time is limited and valuable. U.S. Pat. No. 3,046,978 teaches the use of balls placed within the reservoir to limit the ability to squeeze the reservoir completely, thereby limiting the volume expelled. This design appears to be impractical, as the volume displaced by the balls would decrease the available volume for the patient or cause the BVMR to have to be so large as to be difficult to control and work for the user. This design also allows and indicates a volume based on a complete squeeze or compression of the region of the BVMR chosen and does not allow for intermediary volumes to be selected, as the user would have to "guesstimate" when to stop their compression of the BVMR. Additionally, the movable objects would not allow the user to orientate the bag, or they may be caused to re-orientate the bag as the balls moved within the device. Patent TW201136624 teaches a BVMR with separate reservoirs within one another, each containing different volumes. This construction again defines a volume based on a complete compression of a region of the BVMR but does allow the user to accurately deliver any volume less than the complete volume of the selected chamber. US Patent Publication 2013/01080527 teaches a technique of varying finger position on the outside of the BVMR to cause different volumes to be expelled. The technique relies on a complete compression of the different diameters of the BVMR. This technique would allow for easy user error, as a simple misplacement of a finger would cause a variation in volume delivery. This technique relies on a complete compression to deliver a complete volume as defined by a specific complete diameter of the BVMR, and the user would again have to "guesstimate" when to stop compression of the BVMR to deliver less than the complete volume expected per finger location combination.

SUMMARY

To address one or more of the above-mentioned difficulties, one aspect of the present disclosure is to provide a structure that controls the BVMR so as to allow the user of the BVMR to accurately administer a desired volume. In some embodiments, the desired volume is the recommended volume for a patient as recommended by the American Heart Association and/or appropriate governing bodies by each country.

In another aspect of the present disclosure, the volume to be delivered may be easily adjusted as the patient's condition necessitates.

Yet another aspect of the present disclosure is to provide a BVMR that a provider may be able to use to serve all populations of patients, from infant to adult.

According to some embodiments of the present disclosure, the BVMR may include: a mask configured to make contact with the nose and mouth of the patient in a state not allowing inflow of ambient air; the air bag containing oxygen or air; and a connection hose (or tube) connecting the mask and the air bag, wherein if the air bag is compressed, the oxygen or air contained in the air bag may be supplied to the patient through the connection hose, the mask, and into the respiratory tract of the patient.

In some embodiments, a device to control volume of air delivered by the BVMR comprises a main body that allows opposing wing like structures (i.e., wings) to anchor to each other and to rotate around each other that attaches to the outer aspect of the BVMR by the use of small protrusions (barbs) that puncture the BVMR and rely on the resiliency of the materials used in BVMR construction to provide an anchoring effect for the wings. The wing like structures may follow the curvature of the BVMR. The barb like structures may be located on the wings or the main body, or both, of the device. The wings may have an opening or pass-through that could allow a strap like member to connect to each wing and encompass the BVMR so as to keep the wings in place during use. The wings may be attached in any manner that allows them to stay in place to include but not limited to adhesives, barbs, straps, or simple friction. The wings may be configured so as to consist of, but not limited to, the opposing members, and pin or slide type selector member that when placed would serve as a range of motion limitation device (other embodiments will become evident to those skilled in the art as any structure or combination that allow for control of the range of motion of the wing like members, such as a slide member may be used), and so that at least one wing, or the main body of the device would have a multitude of volume selection/range of motion limiting indicators. The other wing may be formed to have a channel or channels, or other shape (such as stair stepped groove, indentions, or protrusions formed on the main body of one or more of the wings), that allows the selector device to move until it contacts the end of the channel or channels.

The device to control the range of motion is not limited to this description, and those skilled in the art will understand that other combinations that would control the range of rotation of the members or the control of the range of motion of the structures are possible.

The disclosed device may be constructed of plastic, a thermoplastic elastomer, or any other material that would allow for its designed functionality. The material may provide a defined range of motion, which would result in a direct correlation to limit and control the movement of the walls of the BVMR.

In some embodiments, the range of motion is defined and may be simply adjusted by adjusting a selection member of the device. The result may be a new, selected range of motion, and a new, selected volume administration.

This device may be made specifically rigid, semi flexible, articulated or articulating, or even flexible so long as the parts allow for the definition of range of motion.

The device may have contours or be texturized to allow the user to better grip the device.

The device may be configured to allow strap, bands, loops or any other securing device to be placed so as to hold the device to the users hand (possibly around the fingers of the user).

The volume selector may be anywhere on the device so long as it controlled the range of motion of the device. Typically, the volume selector will be placed on the main body of the device where the two wing like structures anchor together, or on the face of the main body (hinge like structure) of the device.

The main body or hinge like structure may be in any configuration so that the wing like members hold together and rotate around each other or oppose each (such as a living hinge).

The main body or hinge like structure may be configured with the use of a tensioning device or pneumatically to control the rate of movement of the wings so as to control either or both the rate of compression of the BVMR and the rate of re-inflation of the BVMR.

The wing like structures may have markings or structures to indicate suggested finger placement.

A selector pin or slide may be provided on one of the wings that folds or bends for placement or may be provided as a separate piece that is coupled as part of an assembly. The selector pin or slide may be formed as part of the device, or removably connected to the device.

The range of motion controller may be formed and over molded into the body of the BVMR. The device may be over molded into place into the walls of the BVMR.

In some embodiments, the BVMR is formed with a static point or origin, referred to as the range of motion controller or ROMC. The ROMC comprises a specifically placed, consistent, firm, immovable structure thermo molded (or otherwise formed) as part of the BVMR itself. This origin or static point can be a fixed point on, or within the bag that the thumb or fingers are directed to so as to provide a consistent, static placement point. This origin creates a static point on, or within the BVMR, that all other points on or within the circumference of the BVMR have a consistent spatial relationship to. The establishment of this static point allows for specific and repeatable movements/distances (distance to volume correlation) for every other point on the circumference of the BVMR, or any point within the BVMR. This may be accomplished by printing on, marking in any form, or thermo molding (injection molding, or any other suitable manufacturing process) a single designated point or region on the bag, or at least one protrusion (wedge) on, outward, or inward from the wall of the BVMR toward the center of the BVMR.

In some embodiments, the controller may be configured so that the thumb or fingers of the user will brace on the outer aspect of the wedge, and the remaining fingers or thumb will rest on the BVMR as normal. This point, region of the wall of the BVMR, or protrusion would act as "blocker" or stop for the fingers or thumb of the user of the BVMR. The user could brace the thumb of the bagging hand on the wedge (as it may be part of the wall of the BVMR) and demarcations may or may not reside on the wall adjacent to the wedge indicating expected volumes or percentages of the total volume of the BVMR (for example, 30% 40% 50% —the user would use the total volume of the BVMR and calculate the amount expected by percentage of movement versus the total volume of the BVMR; for example, 30% would indicate a 30% range of motion, and/or a 30% expulsion of the total volume of the BVMR). Each demarcation would reside slightly farther away from the internal structure, and, therefore, as the user placed their finger or thumb on each different volume marker, the effective range of motion may be increased. The user would increase or decrease the volume selection by rotating the BVMR axially as opposed to moving his or her hand along the length of the BVMR to gain or reduce volume. Multiple planes of protrusions and demarcations could exist but, preferably all points would reside on a single plane across the midsection of the BVMR, or on the plane of normal use. This would result in greater or lesser volume expulsion dictated by the distance the moving fingers or thumb rests away from the wedge. The range of motion demarcations may be mirrored or reside on both sides of the BVMR so as to accommodate left handed or right handed usage of the BVMR. The wedge may be at least one fixed, immovable object on the inside of the BVMR that would act as a stopping point for the moving fingers or thumb of the user of the BVMR. The wedge may be of any shape or size so long as it acts to stop the range motion of the users fingers or thumb. Multiple wedges can be formed in relation to a master wedge at the various volume indications. Each wedge when brought together with the main wedge would result in a calibrated volume expulsion. Multiple wedges can be formed on the interior of the BVMR and the gaps between them can be defined to allow specific ranges of motion to allow the expulsion of various volumes. The gaps may be calibrated to allow an ADULT, PEDIATRIC, or INFANT volume to be expelled. Due to potential limitations of thermo molding, and the risk of malformation of the wedge, the structure(s) may be formed as semi-hollow yet firm so as to create a structure that will cool appropriately during manufacture. The outer aspect of the wedge(s) may be contoured to provide better grip or bracing of the users hand or fingers. A connective member may be placed to help hold the BVMR to the users hand.

In some embodiments, the wedge device may be formed as part of an assembly into, or onto the BVMR. The BVMR may be blow molded (or otherwise constructed) with a pouch or receptacle space formed to receive the separate wedge piece. The wedge piece would then be inserted into the pouch and secured by any means including but not limited to friction creating design, adhesive, straps, pins, sonic welding, barbs or any other fastener or fastening device. The pouch may be formed to have a "lip" on the exterior of the opening, which would cradle the wedge in place. The wedge may be hollow or solid, made to be a container, or filled with a gelatin, fluid or air. There may be multiple wedge inserts to provide defined gaps to represent different ranges of motion and different volume expulsions. The outer aspect of the wedge may be contoured to provide better grip or bracing of the users hand or fingers. A connective member may be placed to help hold the BVMR to the user's hand.

In some embodiments, the range of motion controller may be an insert that is placed entirely within the body of the BVMR. The insert may be soft or flexible, or it may be a hard and rigid component. This insert may follow the curvature of the inner aspect of the reservoir and encircle the cavity using friction to hold in place. This embodiment may be formed from a light-weight and flexible material such as, but not limited to: silicone, rubber, plastic, foam. This insert may have at least one firm or rigid member to act as a stopping point as previously described as the wedge, or it may have multiple protrusions to establish gaps as previously described for the molded embodiment. It may be foam or any other material that would allow for it to be inserted and placed within the BVMR and not impede the ability of the user to use the BVMR appropriately. This structure may attach to a securing member that spans from the inlet to the outlet of the bag (a firm structure, possibly tubular that spans the bag to provide an anchoring point for the wedge or range of motion control device), it may be formed to snuggly fit within the cavity of the reservoir so as to use friction to hold in place, it may be cemented or otherwise glued or connected, it may receive a fastener that secures from outside of the reservoir. The rigid form of the insert may be constructed of a more firm or rigid material such as low-density polyethylene. This version of the insert can be cemented, glued, or otherwise fastened in place either permanently or removably. Potential fasteners include but are not limited to screws, barbs, pins, or nails. These fasteners may extend through the wall of the reservoir (puncture) in order to hold the insert in a fixed position in relation to the reservoir.

The range of motion controller is calibrated according to the material, construction method, brand, or size of BVMR (for example, AMBU, PORTEX, LAERDAL or adult, pediatric, infant) according to the distance-volume correlation.

In accordance with some embodiments, in order to ensure that proper tidal volume is used and a patient is not provided greater than appropriate volume, first the correct volume must be determined. AHA guidelines recommend only enough volume be delivered to barely cause chest rise and fall of the patient, or 6-8 mls per kg. For sake of example only, a BVMR may be marked in 100 ml increments ranging from 100 ml-800 ml. With the device of the present disclosure, a volume appropriate for the patient may be determined (6-8 ml per kg estimating weight of the patient), for example 400 mls, and administered to the patient as normal. If rise and fall of the chest occurred, the user could reduce the selection to 300 mls for the next breath. If rise and fall of the chest is absent, the user would then know that 400 mls is the appropriate volume to use and return to the 400 ml marking for the remainder of the incident. He could then relay that dose to the next provider in the event of a switch due to CPR roles changing, and furthermore to the hospital if and when patient transfer occurs. This would ensure that the patient received the appropriate volume of air/oxygen throughout his care. This would result in much safer patient care than presently possible.

Every different point on the BVMR will result in a different volume administration. Areas between demarcations can be used, and a relative accuracy would exist.

BRIEF DESCRIPTION OF THE DRAWINGS

FIGS. 3A and 3B are exploded views of the range of motion control device of FIG. 1.

DETAILED DESCRIPTION

Figure 1:
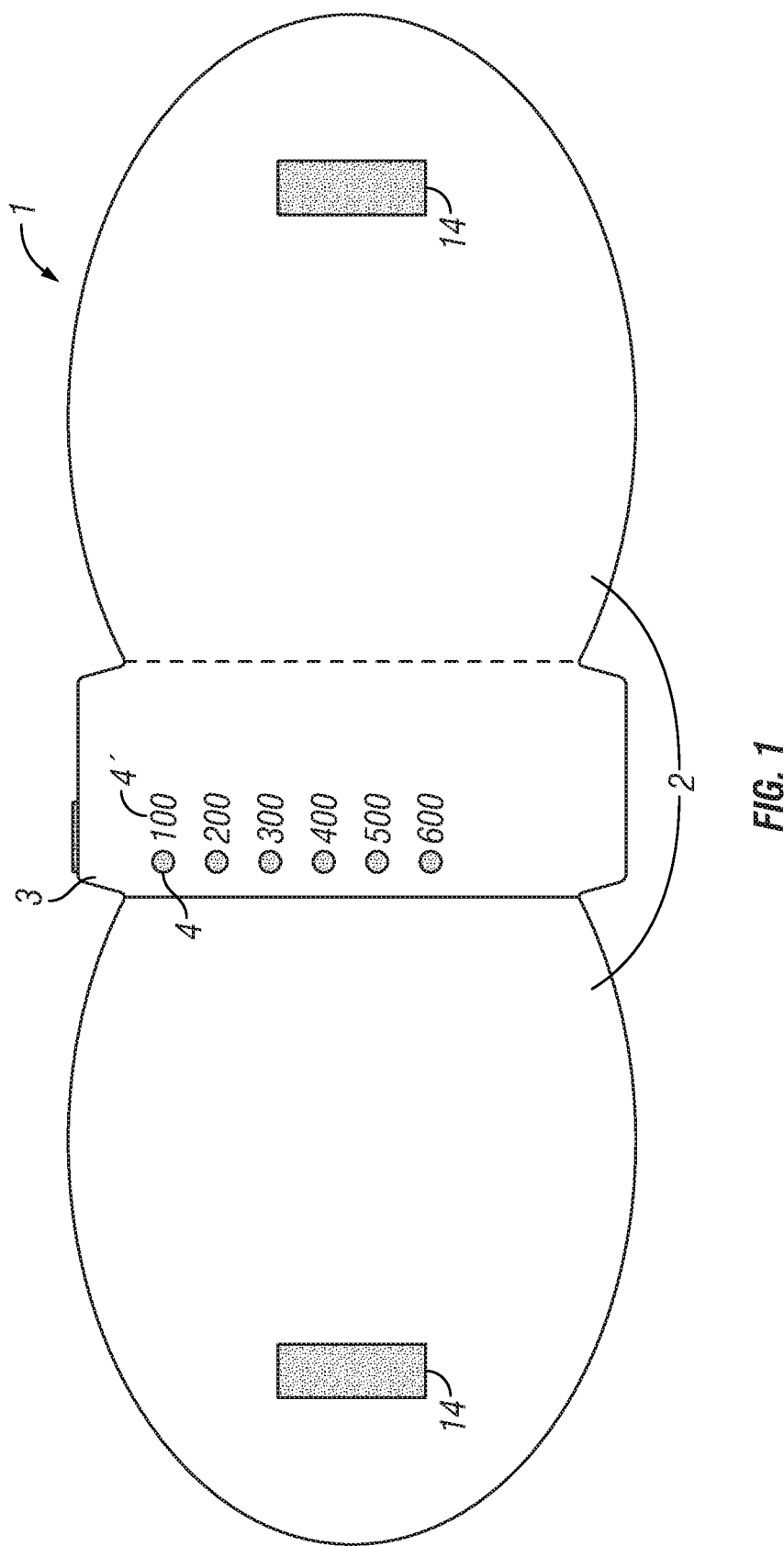
FIG. 1 is a front view of an embodiment of a range of motion control device with a wing like structure.

While the present invention has been particularly shown and described with reference to the accompanying drawings according to exemplary embodiments, the present invention is not limited thereto. It will be understood by those of ordinary skill in the art that various changes in form and details may be made therein without departing from the spirit and scope of the present invention.

Referring to FIGS. 1-5, an embodiment of a range of motion control (ROMC) device comprises a wing like structure 1 comprised of at least two opposing members (or wings) 2 that anchor or secure together and allow each other to rotate at a main body 3. The main body 3 has at least one member with a channel or channels 5 and 5' with varying lengths or widths that allow a corresponding selector placement hole/recipient orifice(s) 4 to slide in line with the channel 5 or channels 5' or other range of motion defining structure such as a stair stepped construction on the main body of the device that specifically limits and defines the range of motion of the opposing wings 2, or any other size or distance differentiating design or construction. The design also having a wing like structure 1 with a series of selection points denoted by selector placement hole/recipient orifice(s) 4 and volume indicators 4' that allow a pin or selector piece or pin 6 of any shape to be placed so as to select a specific volume or range of motion indicator 4'. The selector piece or pin 6 extends through the placement hole/recipient orifice 4 and resides in the desired channel 5. When the wings 2 are operated and moved toward each other, the selector piece or pin is allowed to move within the channel 5 until it reaches the end of the channel, effectively controlling the range of motion of the device, and the volume ejected from the reservoir. The selector piece or pin 6 may be formed as part of the wing member or as a separate part. Potential connections or openings 14 for straps are shown.

Figure 2:
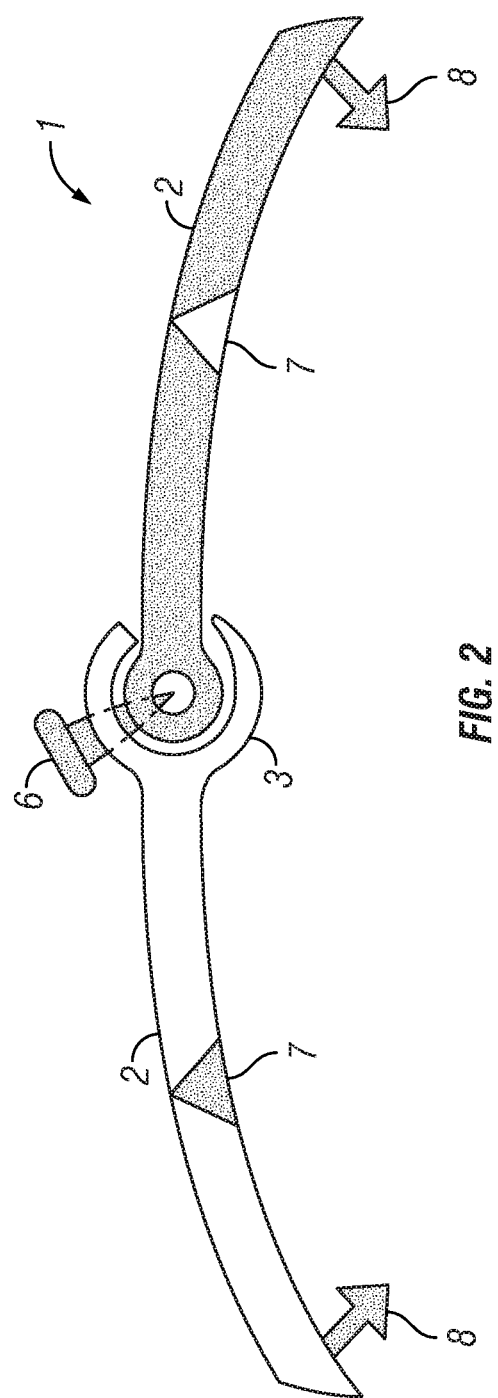
FIG. 2 is a front view of the range of motion control device of FIG. 1.

FIG. 2. depicts the frontal view of the wing like structure 1. The wings may be curved so that they match the curvature of the BVMR 9. FIG. 2 also shows that the wings 2 can be formed with hinge like points 7 or be made to articulate to accommodate the construction process. This use of articulating points 7 in the design simplifies the manufacturing process (e.g., if injection molded, the tooling is simpler since the item can be molded in a flat plane). The small living hinges would allow it to take the appropriate shape of the bag when the user attaches it to the bag. Preferably, the wing like structure 1 attaches to the BVMR 9 by having a barb like structure 8 puncture into the BVMR 9 and create an anchoring effect. The wing like structure 1 can be adhered to the BVMR 9 in any manner including but not limited to the barbs 8, adhesives, or strap(s) to encircle the BVMR 9 and hold the wing like structure 1 in place during use of the BVMR. FIG. 2 demonstrates the pin 6 now in place to limit the range of rotation of the main body 3, which translates into a controlled range of motion directly related to the length of the selected channel 5 and placement of the selector placement hole/recipient orifice in relation to the placement of the pin 6 of the wings 2.

Figure 3A:
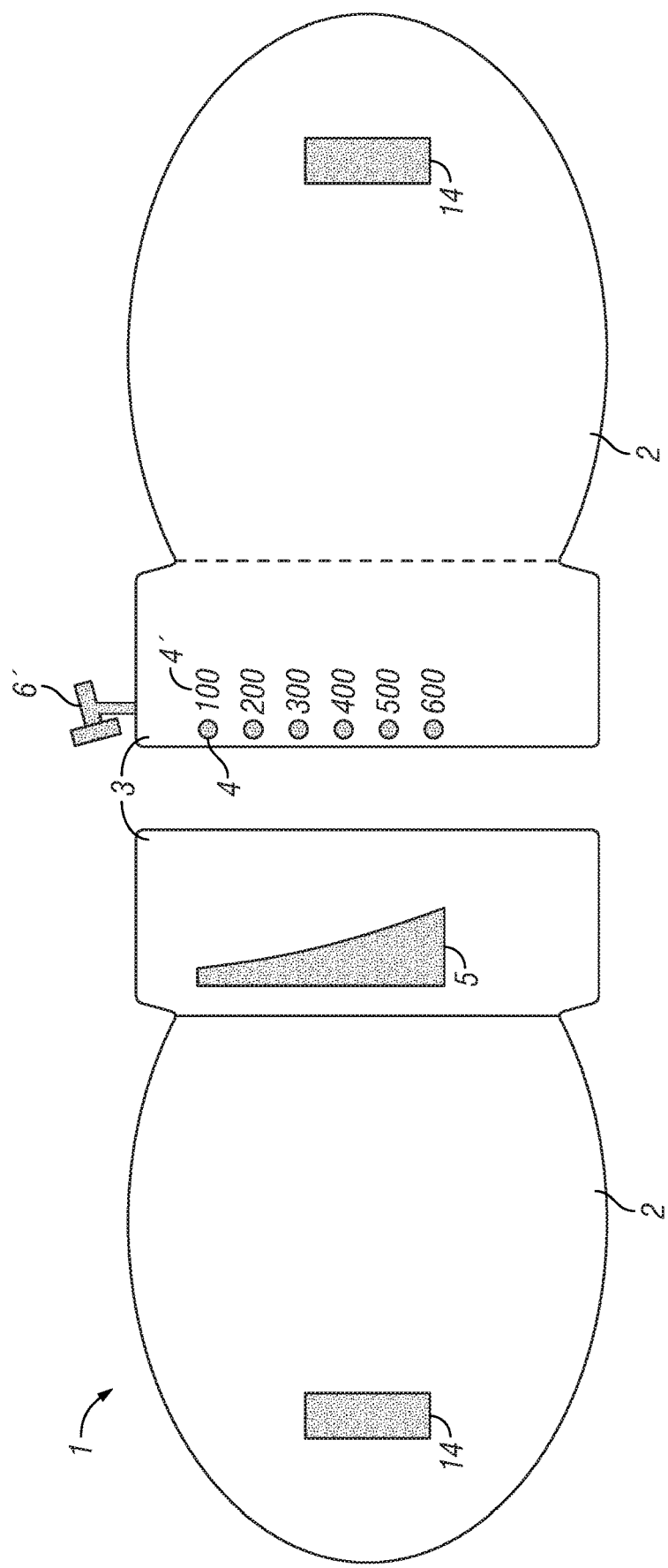

FIGS. 3A and 3B are exploded views of the ROMC device. FIG. 3A illustrates a gradually widening range of motion control channel 5 and the selection device or pin 6' as an integrally formed member. FIG. 3B shows the wing like structure 1 with a second embodiment of the range of motion control channels 5' and selection holes 4 and volume indicators 4'. By having multiple holes or recipient orifices 4 aligned with a single channel 5, a single channel 5 can control multiple ranges of motion and volume administrations. This design would allow for a greater number of choices of volumes to administer.

Figure 4:
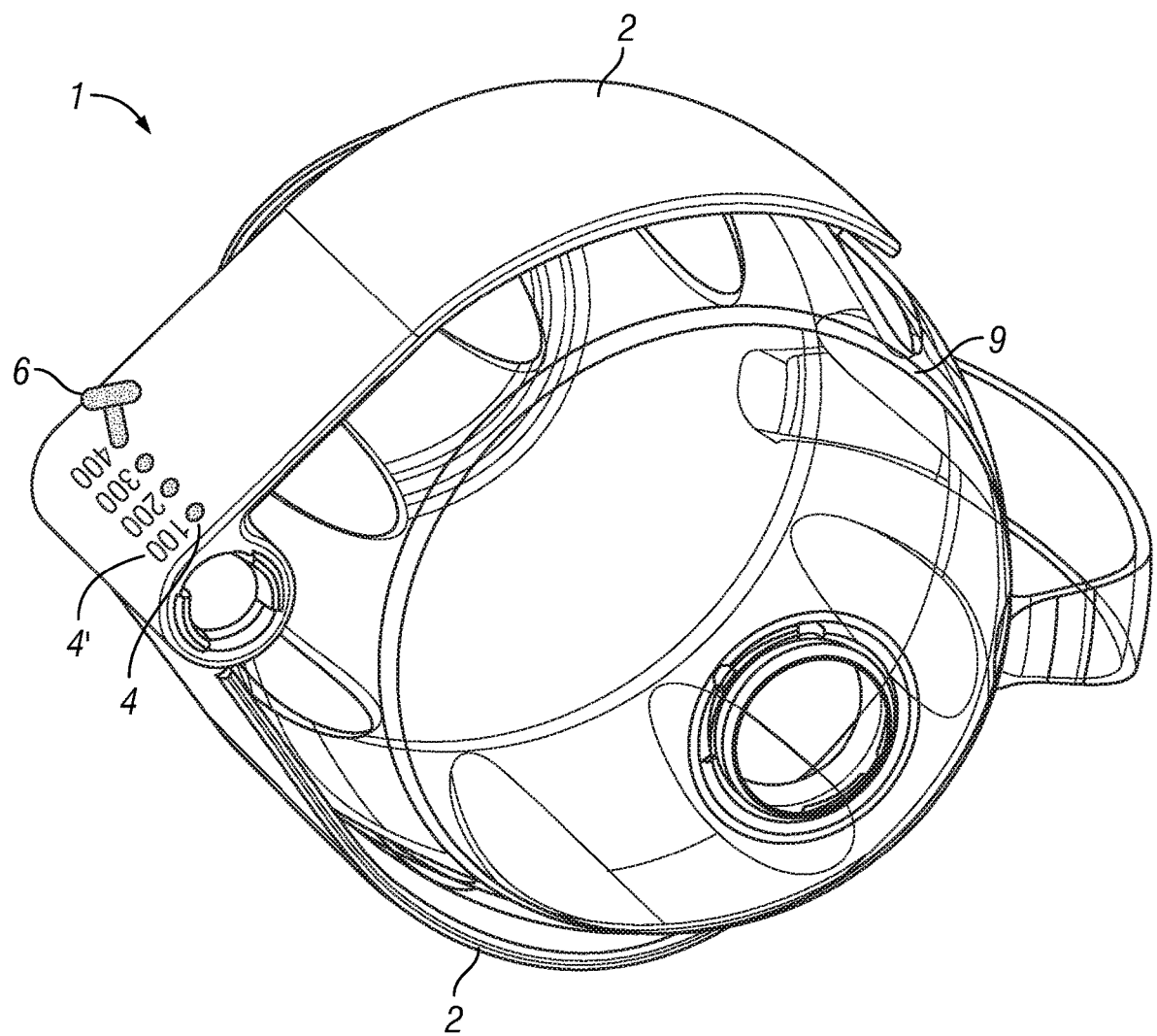
FIG. 4 illustrates how the range of motion control device of FIG. 1 may fit on the BVMR.

FIG. 4 illustrates the wing like structure 1 now attached to the BVMR 9 and being held in place by the barbs 8. The resilient properties of the material used in the reservoir bags 9 cause the material to seal around the body of the barb 8 so that there is minimal or no leakage. In some embodiments, as is known in the art, BVMR 9 can have an output portion coupled to a mask that can fit over a patient's face and output air to the patient.

Figure 5:
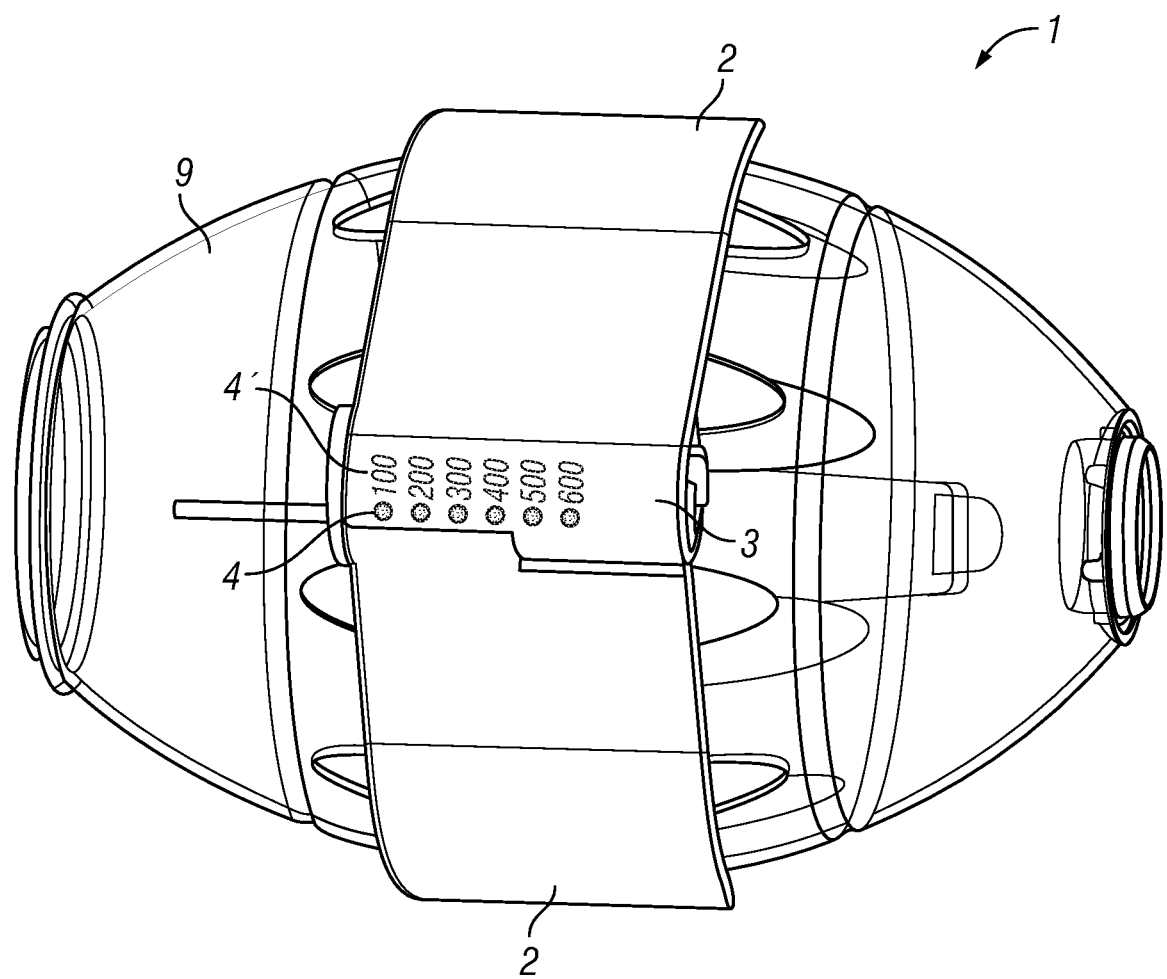
FIG. 5 is a top view of the range of motion control device of FIG. 1 assembled to a BVMR.

FIG. 5 is a top view of the wing like structure 1 fastened to the BVMR 9.

Figure 6:
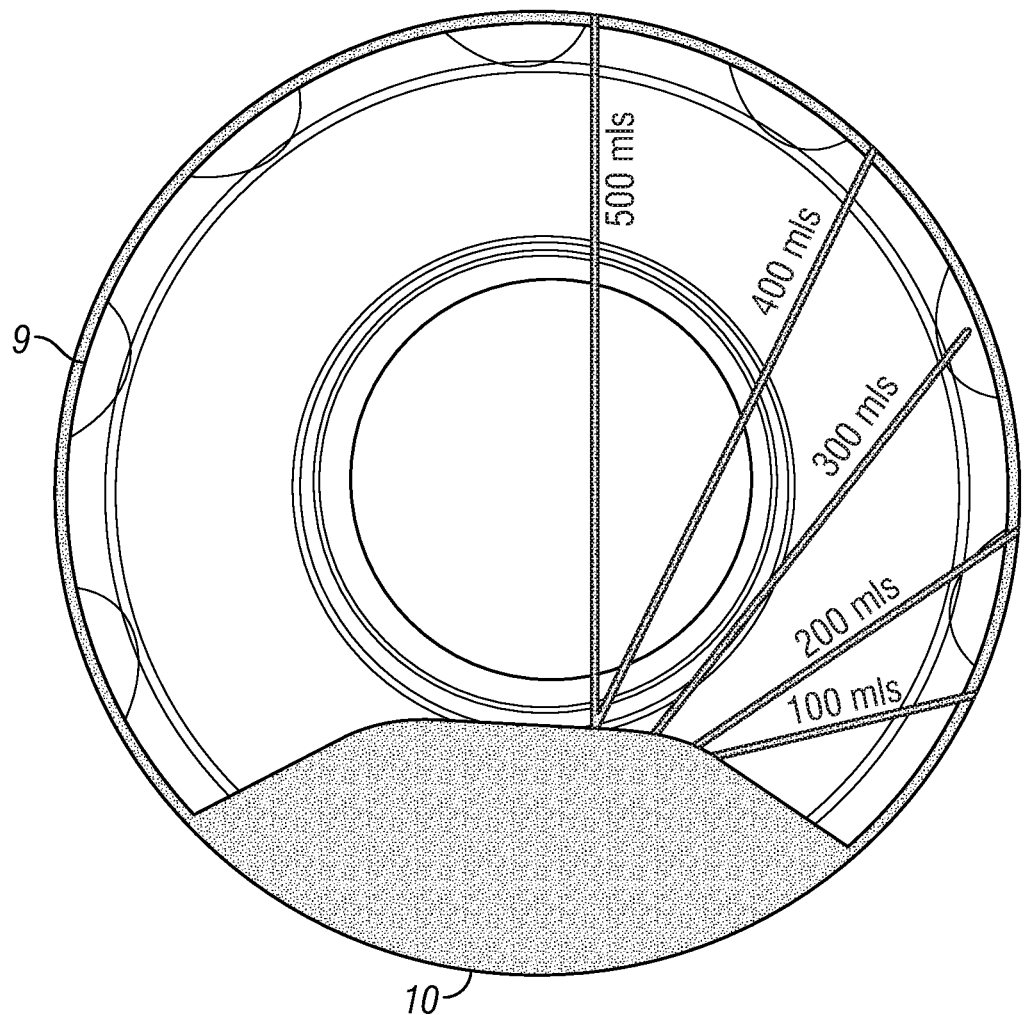
FIG. 6 is a cross sectional view of an embodiment of a range of motion control device with an integrally formed wedge like structure.
Figure 7:
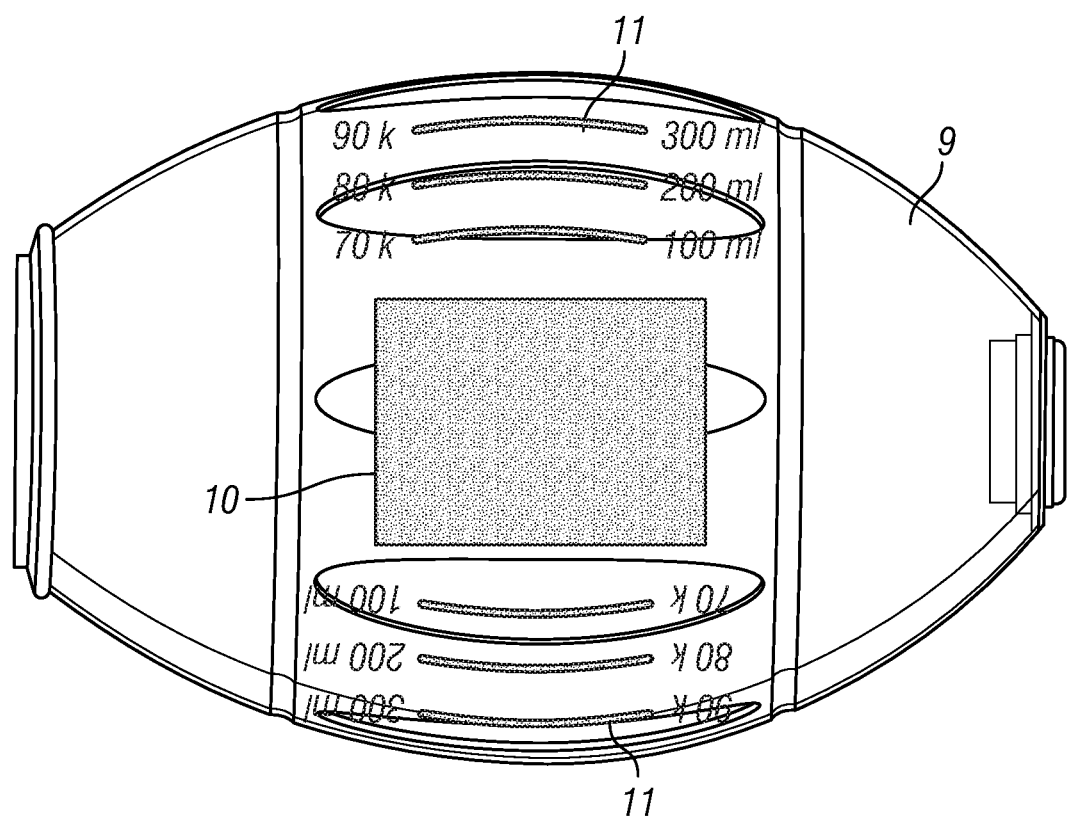
FIG. 7 is a bottom view of the bottom of the device of FIG. 6 with distance-volume selection indicators.
Figure 8:
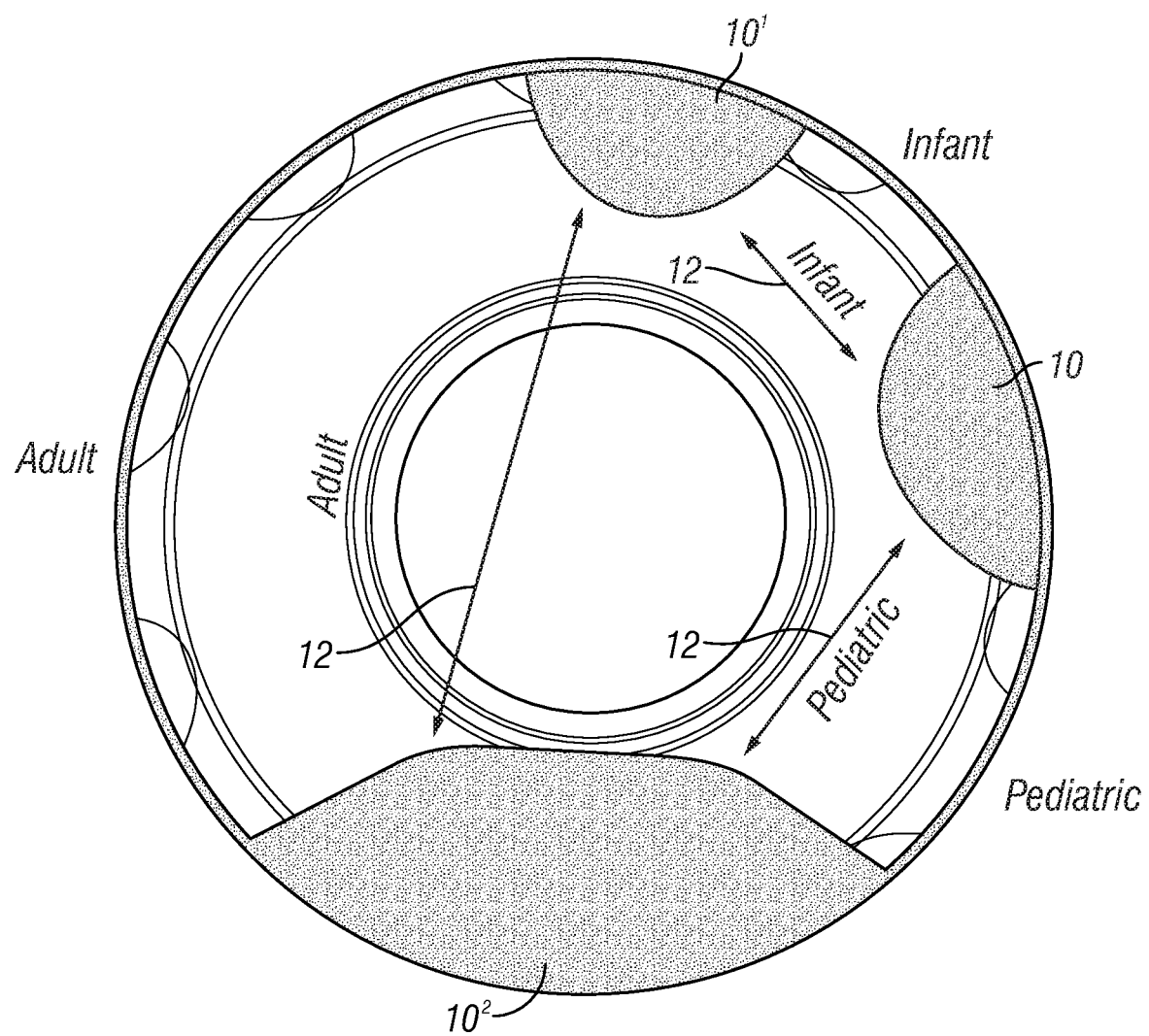
FIG. 8 is a cross sectional view of an embodiment with multiple protrusions.

FIGS. 6-8 depict another embodiment of the device which comprises an integrally formed "wedge" 10 on the interior of the BVMR 9. As used herein, "wedge" means a protrusion. Due to differences in the construction of the different brands and/or the different sized BVMRs (adult, pediatric, infant), the wedge 10 may be of different sizes or shapes to appropriately accommodate the needs of the different sized BVMRs 9. FIG. 6 also illustrates the distance to volume correlation that is the basis for the new design.

FIG. 7 depicts the internal wedge 10 from the bottom aspect. Also illustrated are the mirrored volume selection opportunities that accommodate right or left-handed users.

FIG. 8 is a cross sectional perspective of the BVMR 9 with multiple, and specifically spaced wedges 10, 10', $10^2$. The spaces or gaps 12 between the wedges 10, 10', $10^2$ represent the generic volumes that each individually sized (e.g., adult, pediatric, infant) BVMRs 9 of present day construction contain. The user of the BVMR 9 would simply compress two of the protrusions 10, 10', $10^2$ together to obtain the same functionality and tidal volume administration as present day BVMRs 9 which only have a single defined range of motion and volume administration, the total compression of the BVMR 9. Any volume desired at less than a complete compression of the BVMR 9 would be an undefined guess or estimation. This embodiment may allow a single BVMR 9 to have the three accepted volume capabilities widely accepted today in the field of study, but would rely on the user to control volume as present BVMRs do.

Figure 9A:
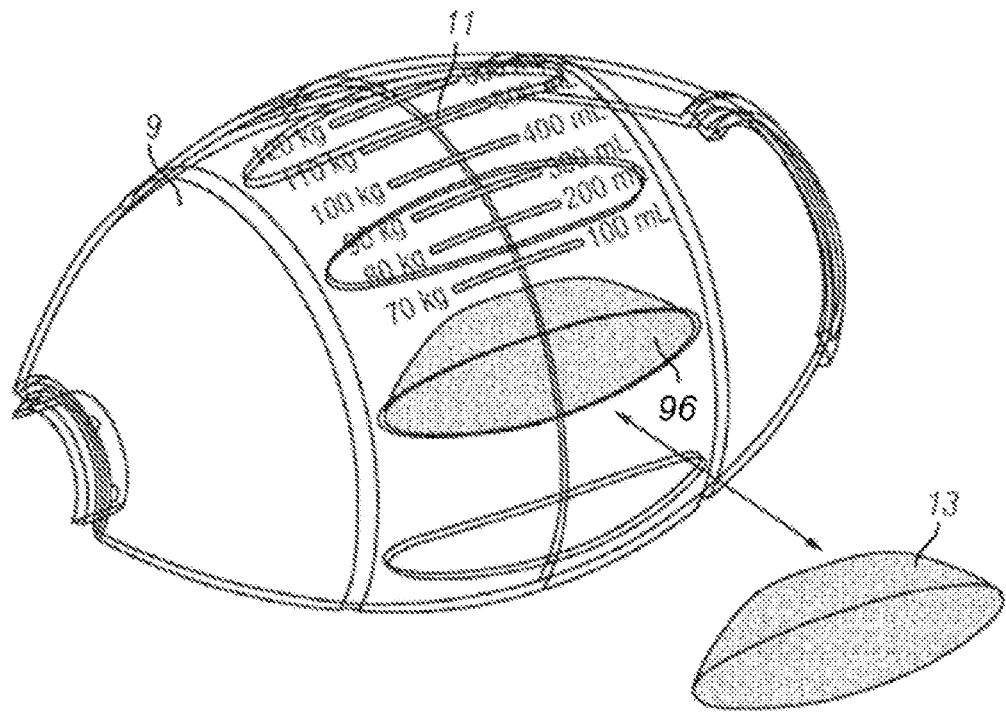
FIG. 9A is a perspective view of an embodiment having a pouch/receptacle for receiving the external wedge.
Figure 9B:
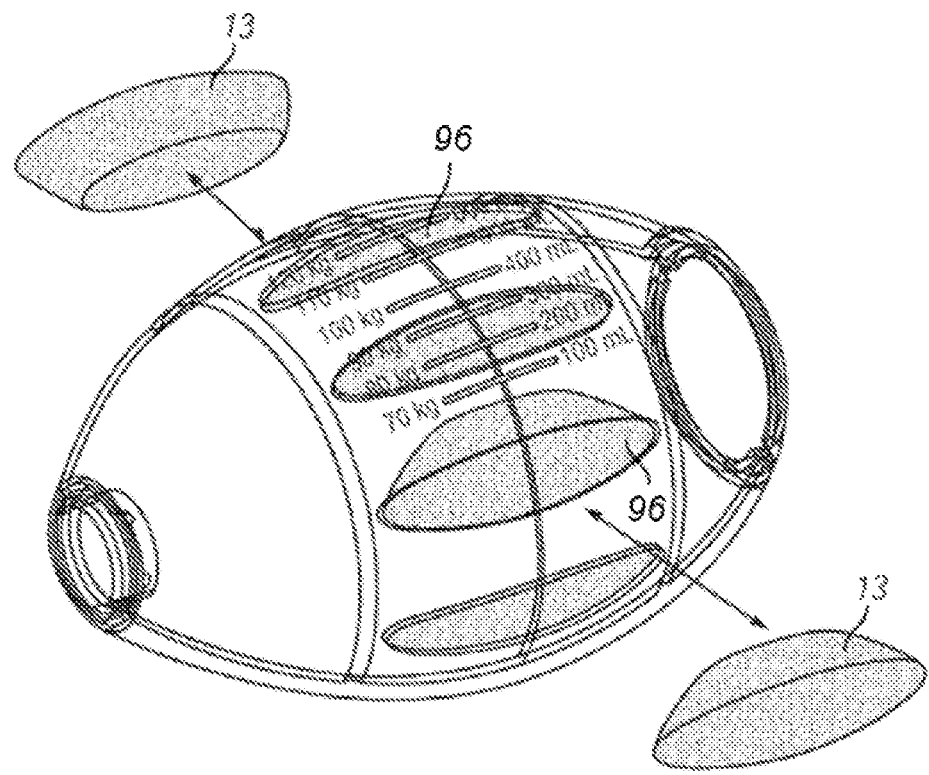
FIG. 9B is a perspective of a multiple external wedge configuration.

FIG. 9 is a perspective of an assembly that would allow the BVMR 9 to be formed with a pouch or receptacle 96 to receive an external piece or wedge 13 to be inserted into it. The pouch 96 would securely hold the external wedge 13. The wedge may be formed with barbs or contours that secure it into place with the pouch 96. Adhesives may be used to secure it into place as well. This embodiment is well suited to BVMRs that use a blow molded construction method rather than an injection molded method of construction.

Figure 10A:
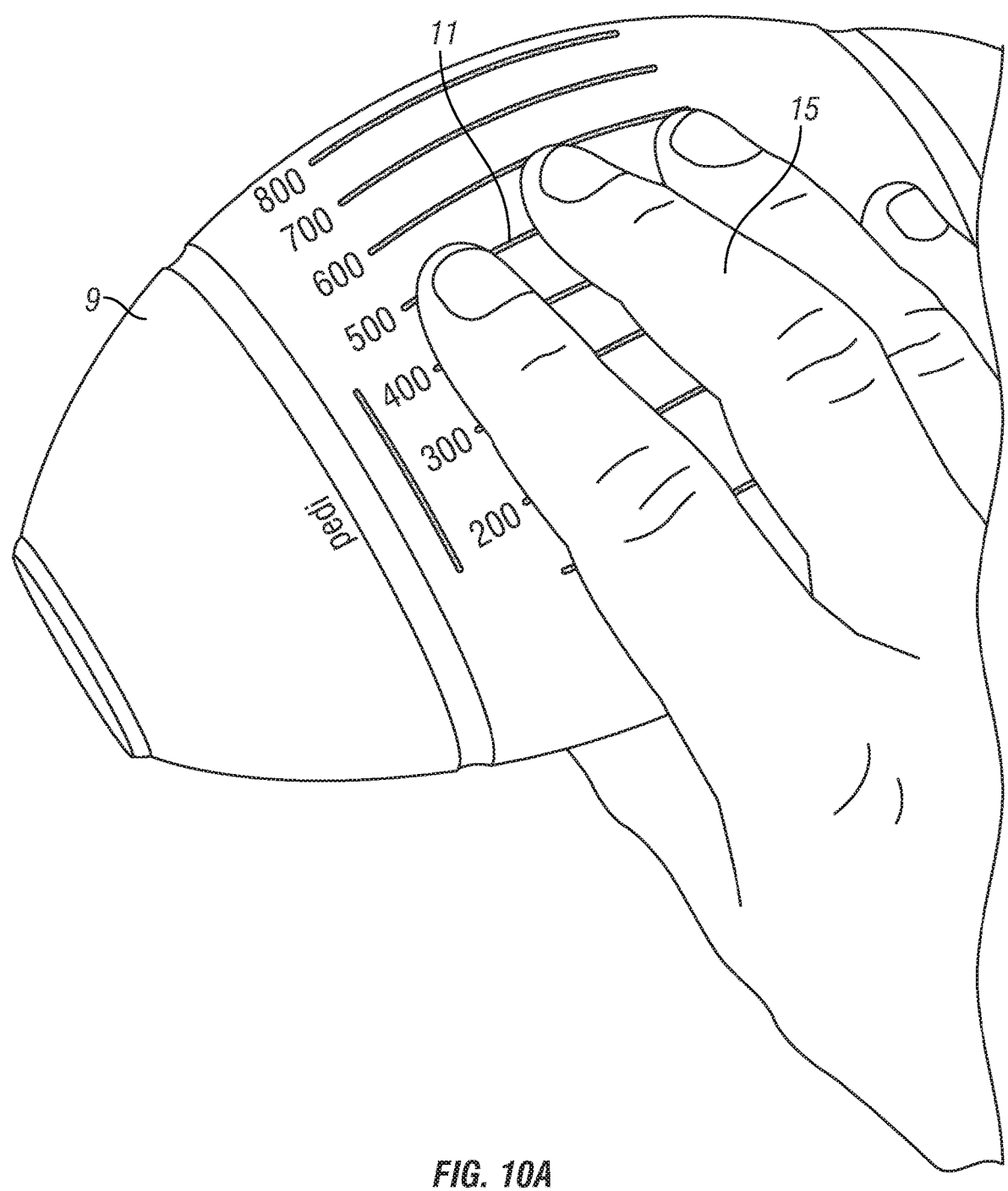
FIGS. 10A and 10B depict a preferred sequence for establishing appropriate volume administration.
Figure 10B:
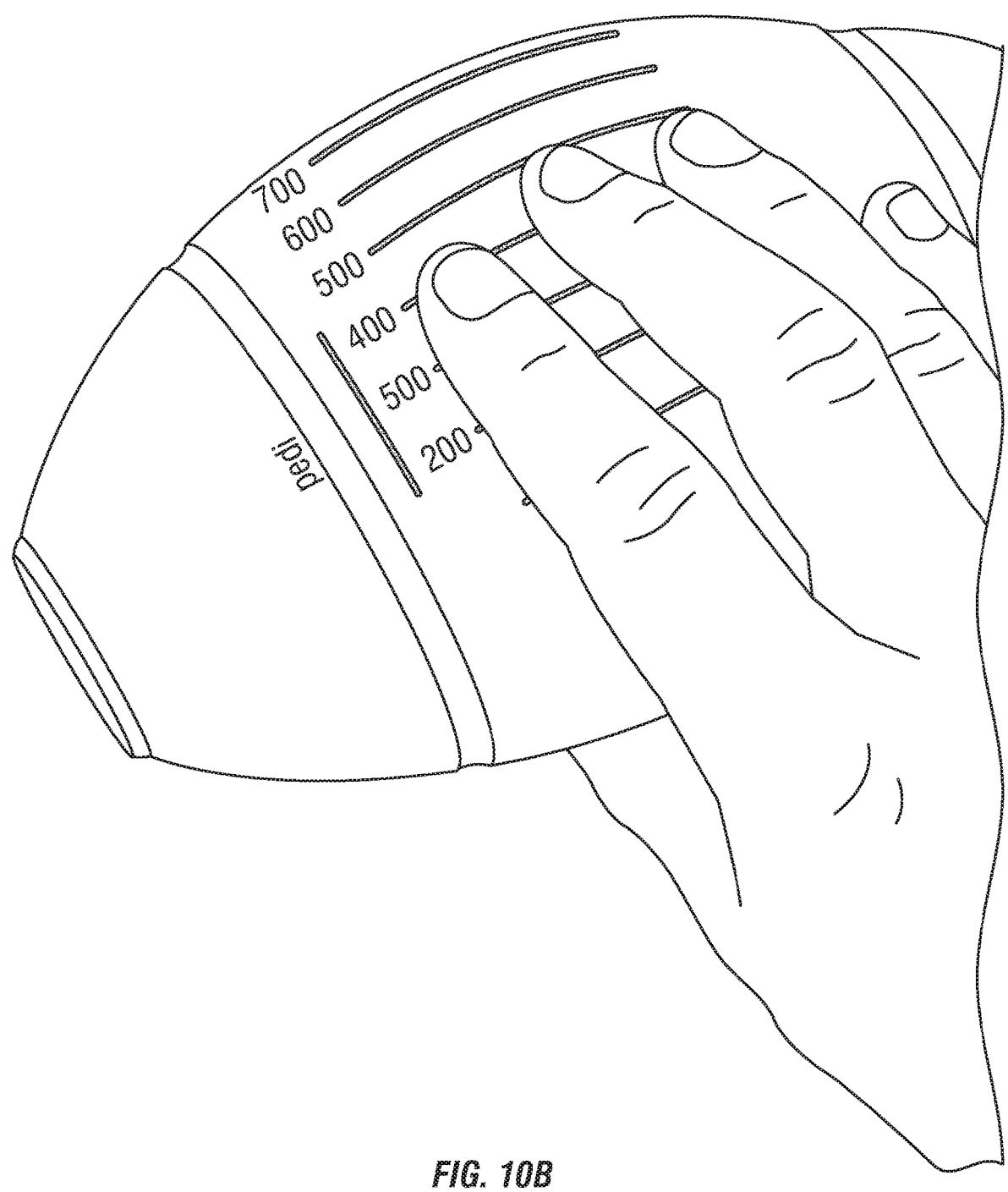

FIGS. 10A-10B depict a method of use of the new device. In the following, it is assumed that all ventilations correspond to the appropriate frequencies for use of the BVMR during any situation. An initial volume is selected in FIG. 10A based on the patient's weight or an estimate of the patient's weight (i.e., 400 mls), and the user places his or her hand, or his or hers fingers 15, at the appropriate volume indicator 11 and delivers a breath by touching his first, second and third fingers to the wedge 10. Note, minor volume differences are delivered if only one or two of the three fingers are used or contact the wedge 10 due to minor differences in the amount of surface area compressed of the BVMR 9. For uniformity and consistent results, it is preferred that the first three fingers of the user all contact the wedge 10. If the user observes chest rise and fall he knows he has at least the correct volume, but perhaps too much. The user moves his hand or fingers 15 to the next lower setting 10B, and delivers a breath. If rise and fall of the chest is still visible, he now knows 400 mls was too much, and he now is administering at least the correct volume. The user repeats these steps until rise and fall of the chest is no longer present. He now knows he is using too little volume and he places his hand back at the last noted volume that caused rise and fall of the patient's chest. He or she can now relay for the patient's records what volume was used to ventilate the patient, as well as to any other provider that may come to ventilate the patient.

Figure 11:
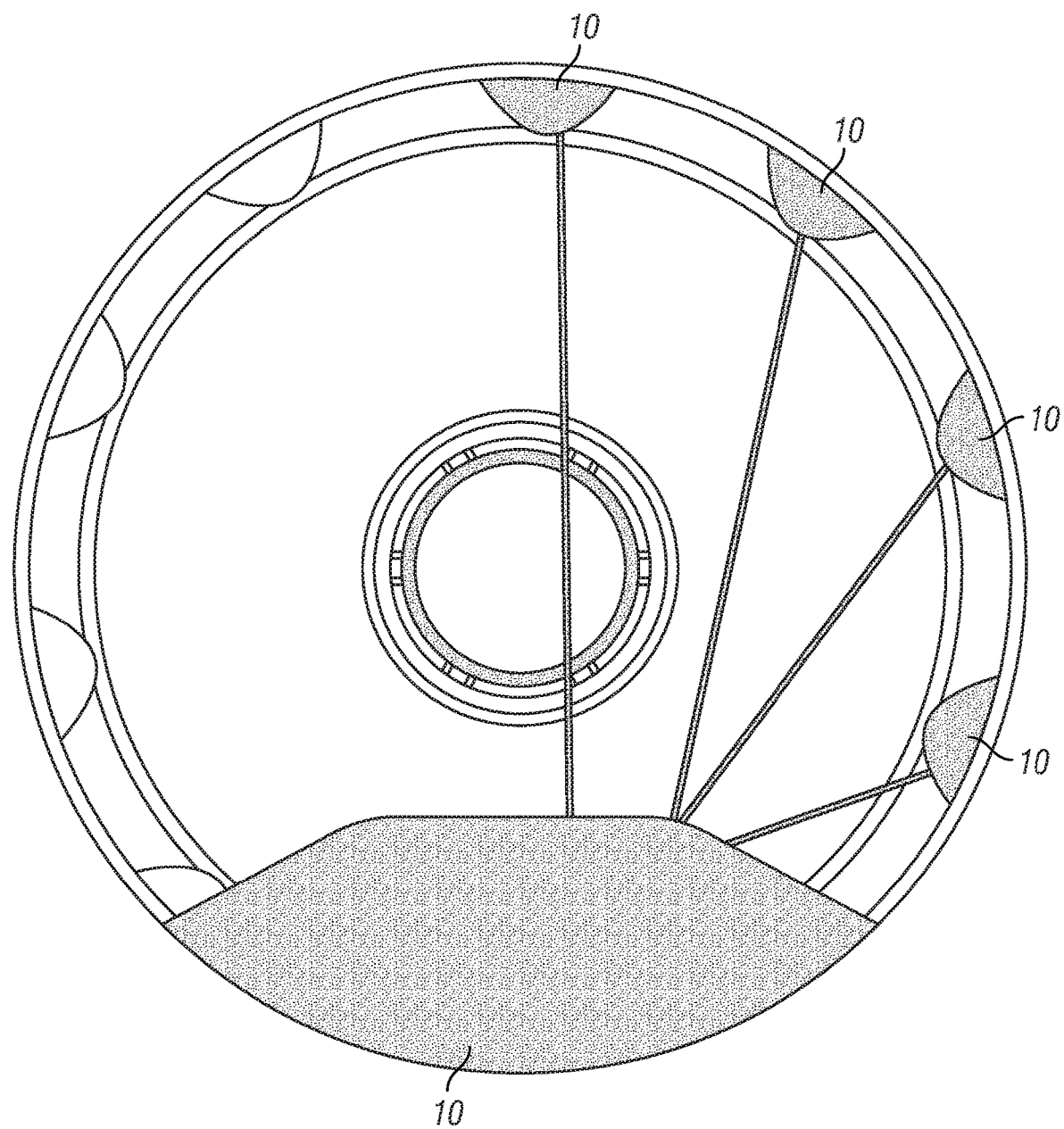
FIG. 11 is an illustration of the distance-volume relationship.

FIG. 11 illustrates a multi-protrusion 10 design that would allow for differentiated distances from various points on the circumference of the reservoir. The protrusions or wedges could have varying dimensions.

Figure 12:
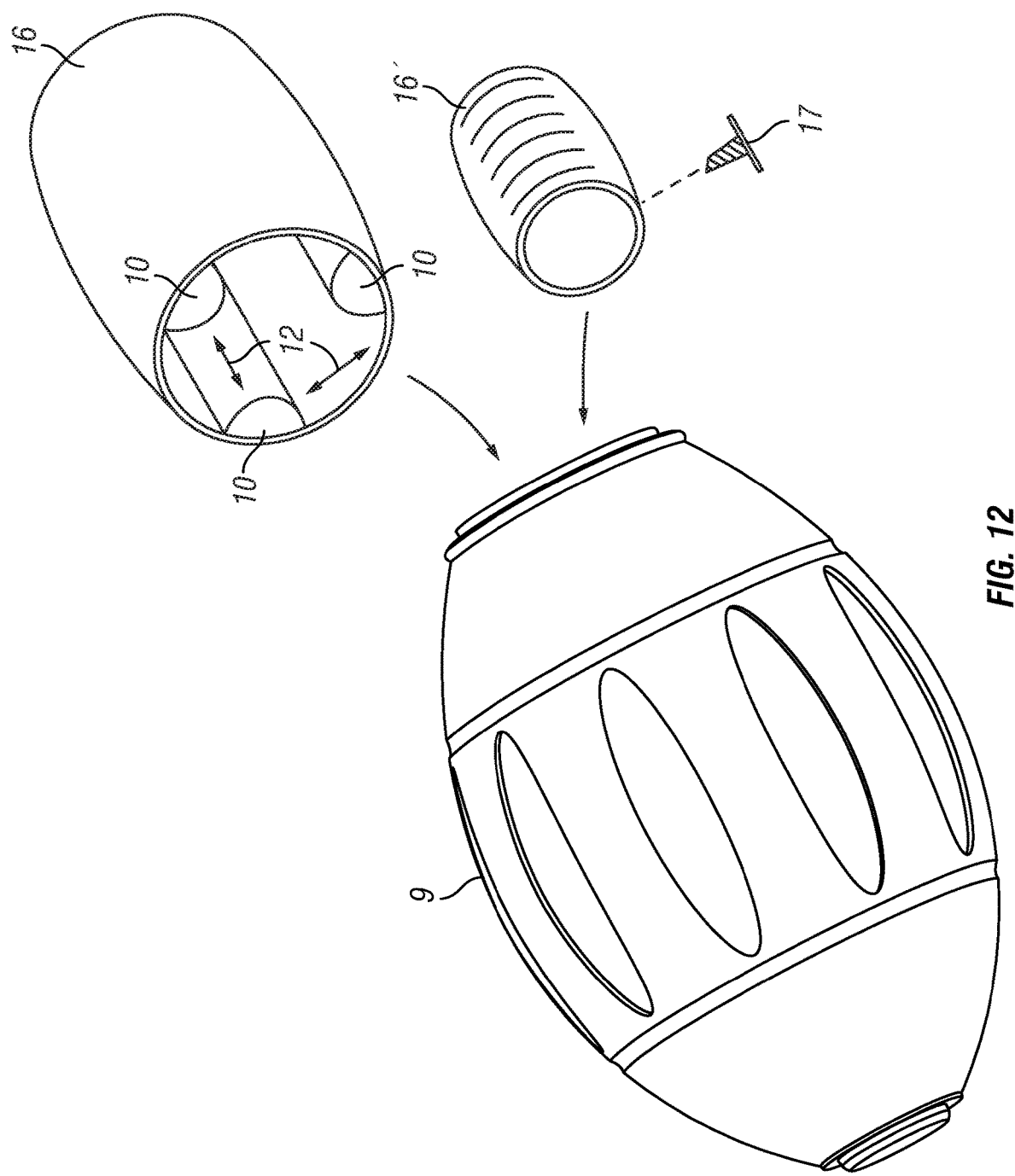
FIG. 12 depicts an insert that may be placed within the reservoir of the BVMR.

FIG. 12 illustrates an insert 16 and 16' that may be placed within the reservoir of the BVMR 9 and fastened in place by at least one fastener 17. The insert 16 may have one or more protrusions 10 or gaps 12, and may be made in a firm manner so as to act as a stopping point for the users hand/fingers during operation of the BVMR. The insert 16 could fit within the cavity of the reservoir bag circumferentially. The insert 16 or 16' may be anchored in place in at least one point in ways to include but not be limited to: friction, fasteners 17, adhesives, screws, snaps, barbs, or attached to the inlet assembly, outlet assembly or both; or to a structure (not pictured) that may span across the bag in any direction to serve as an anchoring point for the insert 16 or 16'. The fasteners may originate from the body of the insert 16 or 16'. The insert 16 preferably may be formed of a silicone or foam that would not interrupt the user's ability to use the BVMR and that would have a constant outward pressure to hold it in place if a fastener is not used. Insert 16' may be a solid, rigid material such as low density polyethylene or polycarbonate, or semi rigid material such as silicone or the like.

Figure 13:
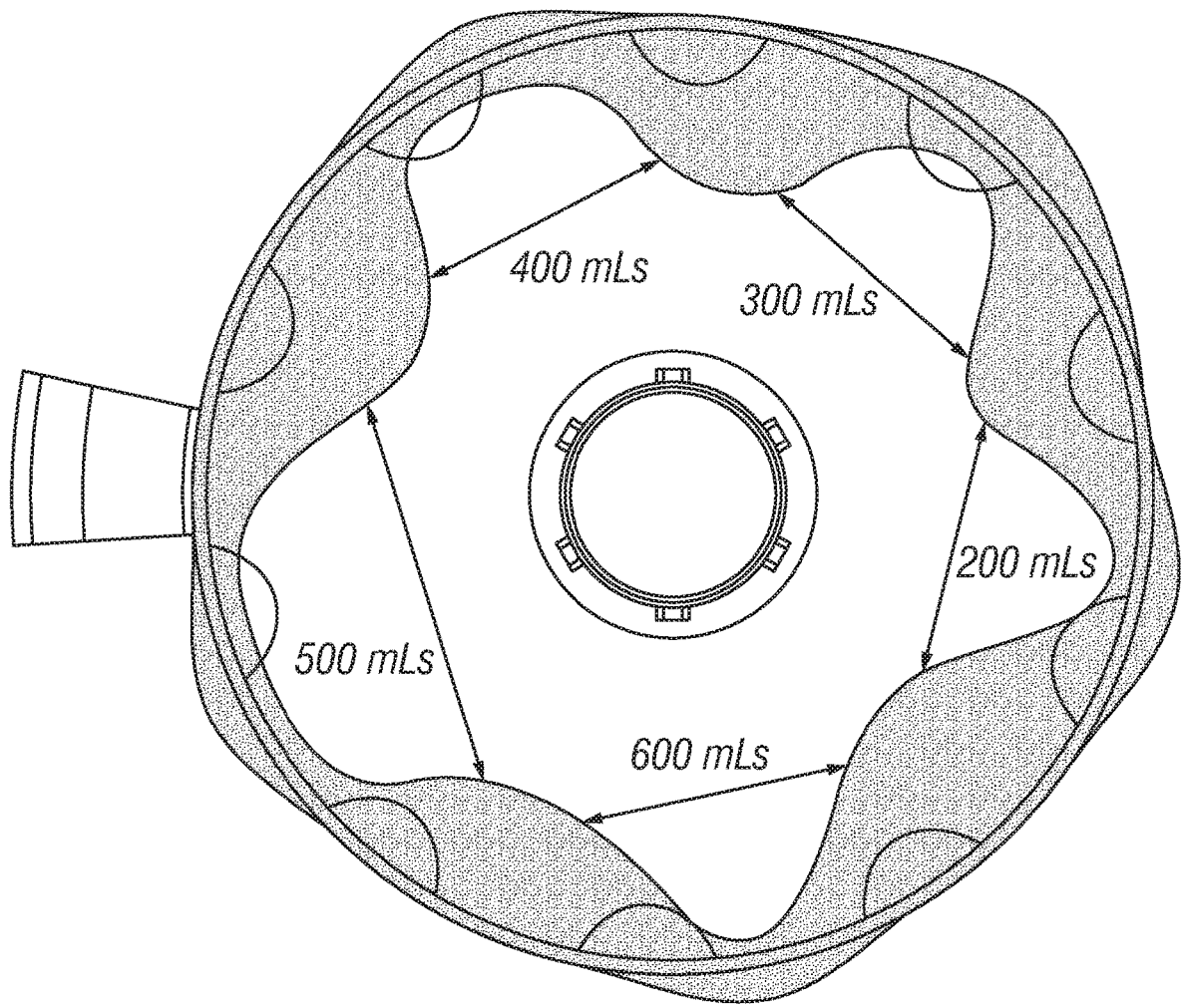
FIG. 13 illustrates a multiple protrusion/multiple gap embodiment of the present disclosure.
Figure 14A:
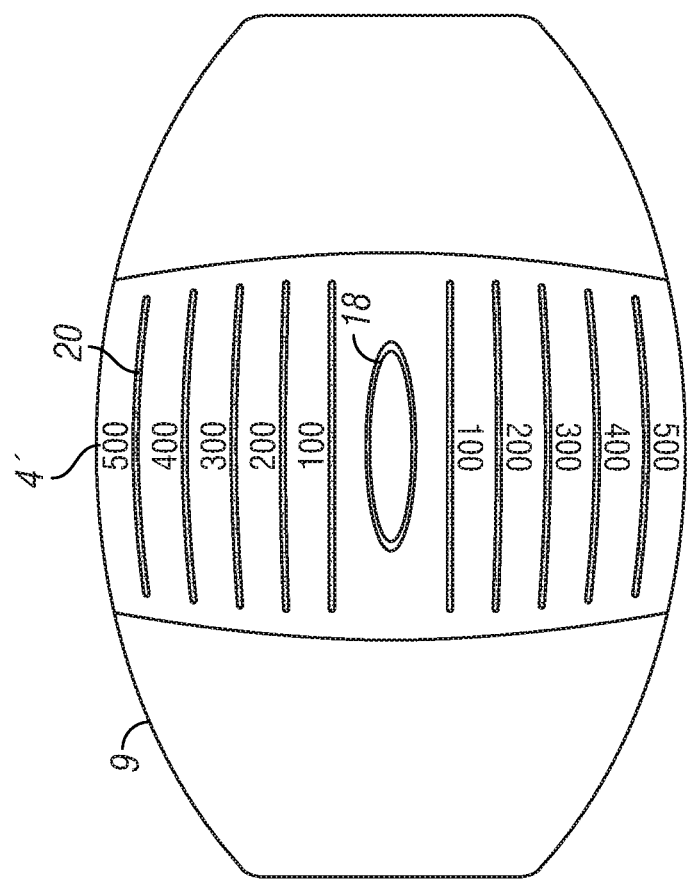
FIGS. 14A-14F illustrate another embodiment of the present disclosure.
Figure 14B:
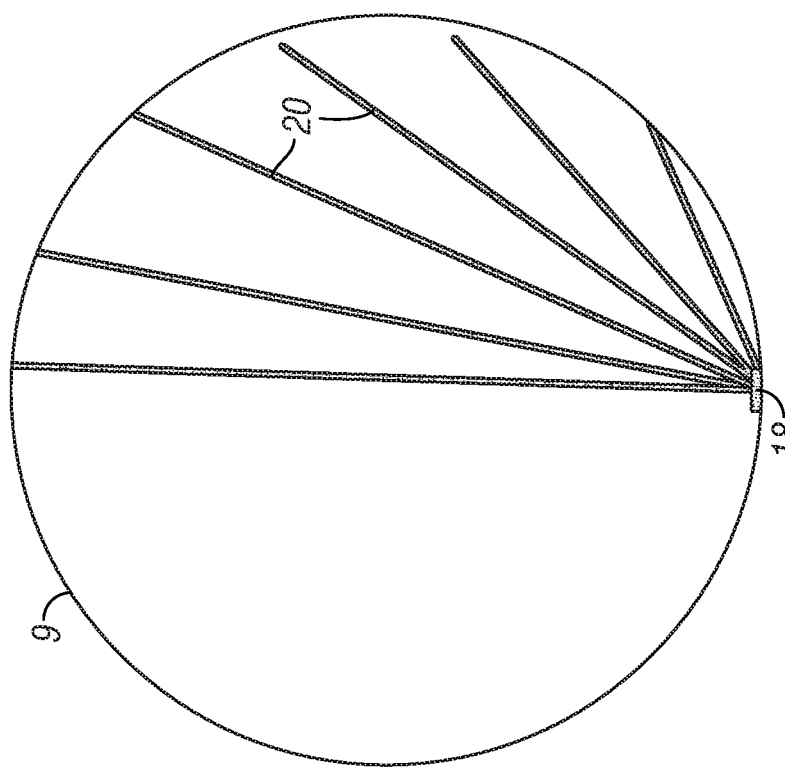
Figure 14C:
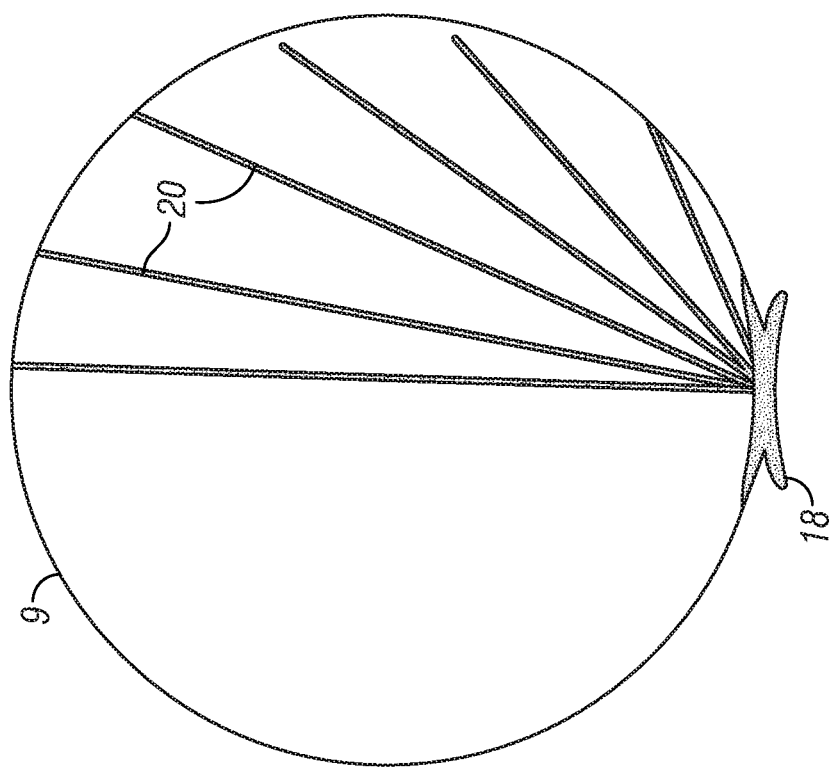
Figure 14D:
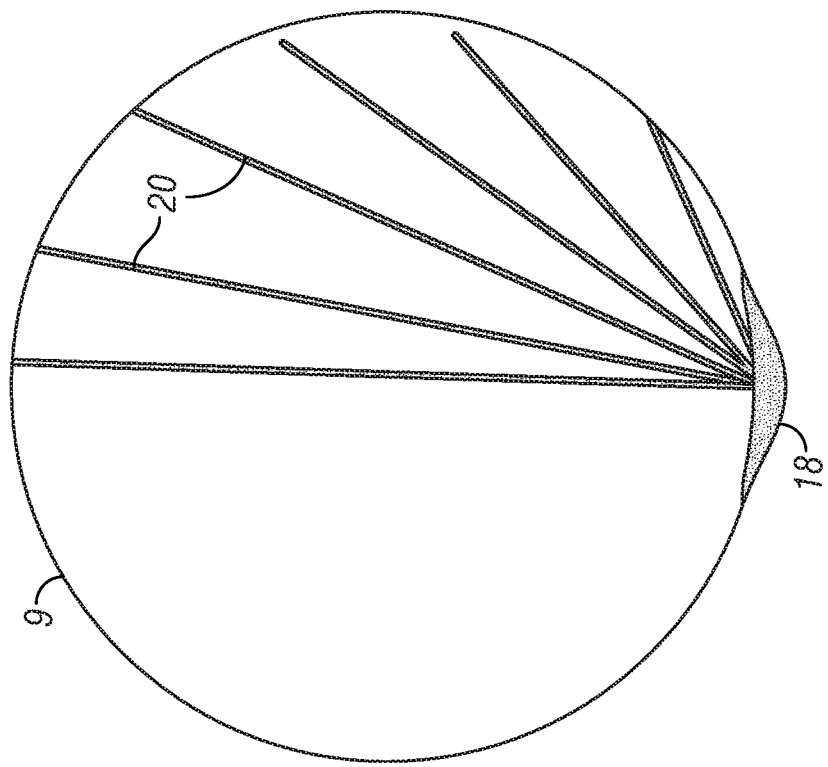
Figure 14F:
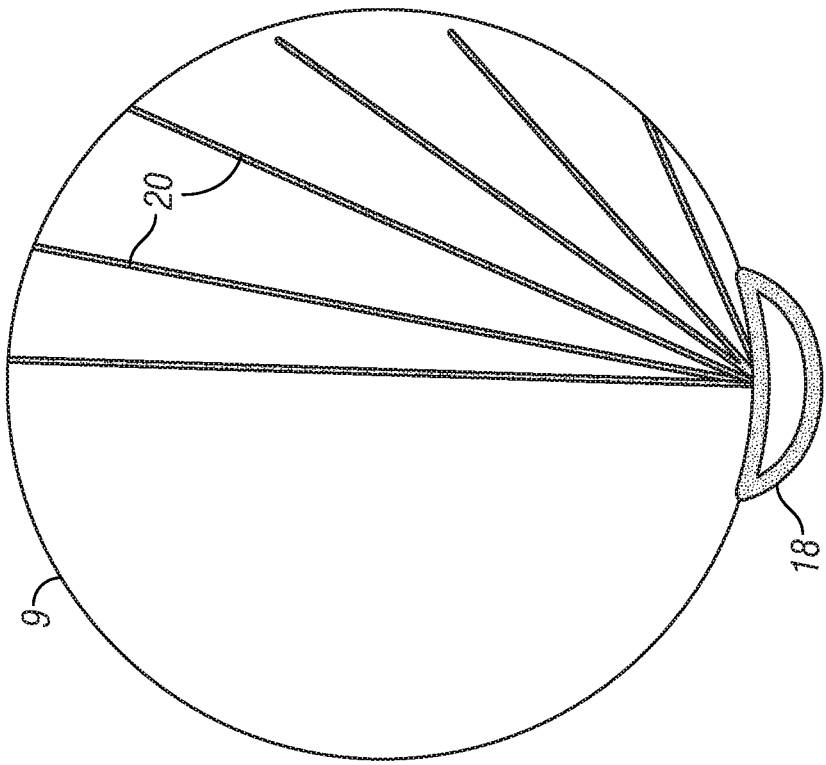
Figure 14E:
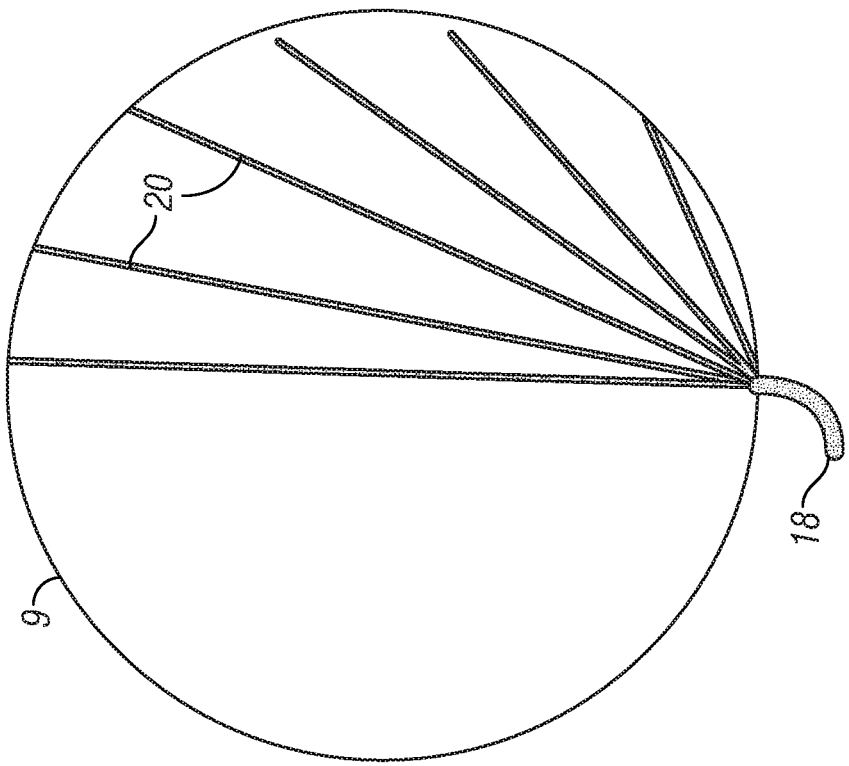

FIG. 13 illustrates a design of the device that may contain more defined gaps 12 that represent specific volume estimates to allow for specific volumes to be administered.

FIGS. 14A-14F illustrate a design of the device which has a static point or origin, referred to as the range of motion controller or ROMC. The ROMC 18 comprises a specifically placed, consistent, firm, immovable structure which is formed as part of the BVMR 9 itself. This origin or static point can be a fixed point on, or within the bag that the thumb or fingers are directed to so as to provide a consistent, static placement point for the thumb or fingers. This origin creates a static point on, or within the BVMR, that all other points on or within the circumference of the BVMR have a consistent spatial relationship to. The establishment of this static point allows for specific and repeatable movements/distances (distance to volume correlation) for every other point on the circumference of the BVMR, or any point within the BVMR. This may be accomplished by printing on, marking in any form, or thermo molding (injection molding, or any other suitable manufacturing process) a single designated point or region on the bag, or at least one protrusion (wedge) on, outward, or inward from the wall of the BVMR toward the center of the BVMR. To use the BVMR, the user places his thumb on the static point. The fingers are then placed a specific distance away from the static point. The precise distance is indicated by indicia on the bag, such as lines 20 and corresponding volume indicators 4'. The user then squeezes the bag to deliver a specific volume of air associated with the finger position. Alternatively, the device may be designed so that the fingers are placed in a static place, and the thumb is moved. The configuration of the ROMC structure 18 may be a bump structure (FIG. 14C), a concave/convex structure (FIG. 14D), a hook shaped structure (FIG. 14E), a loop structure (FIG. 14F), or any other structure to indicate correct placement of, and potentially hold the thumb or fingers at the desired location.

Figure 15:
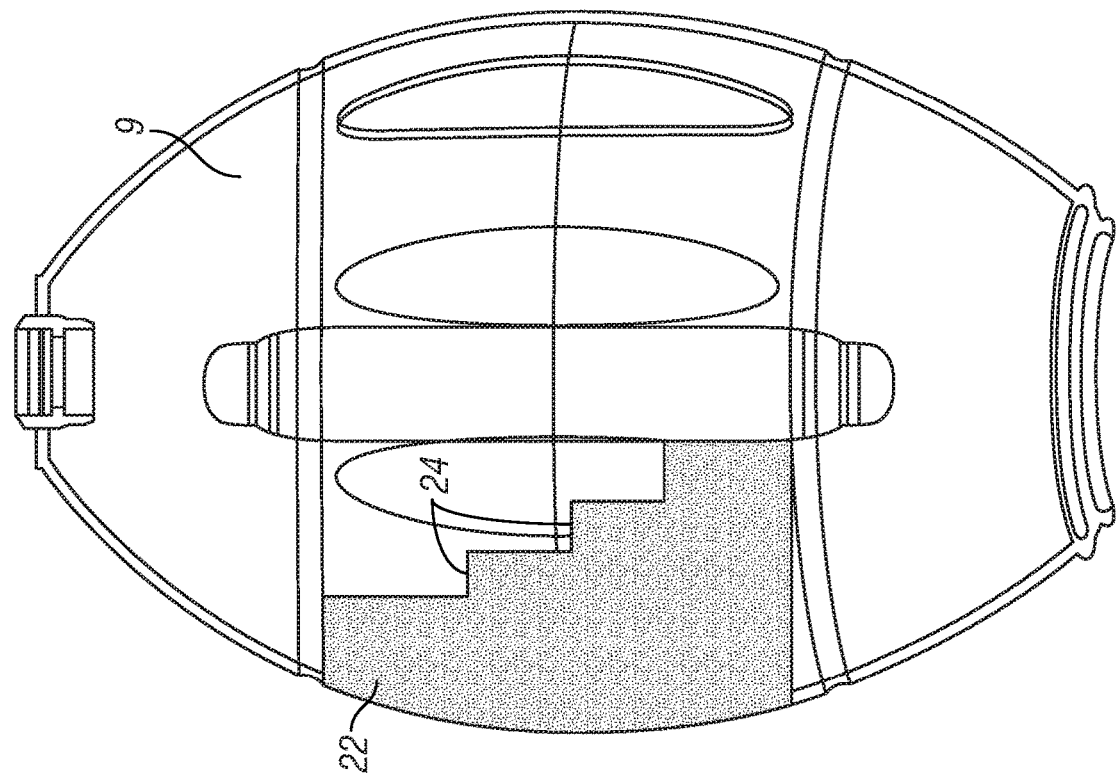
FIG. 15 illustrates a stepped range of motion control device according to another embodiment of the present disclosure.
Figure 17A:
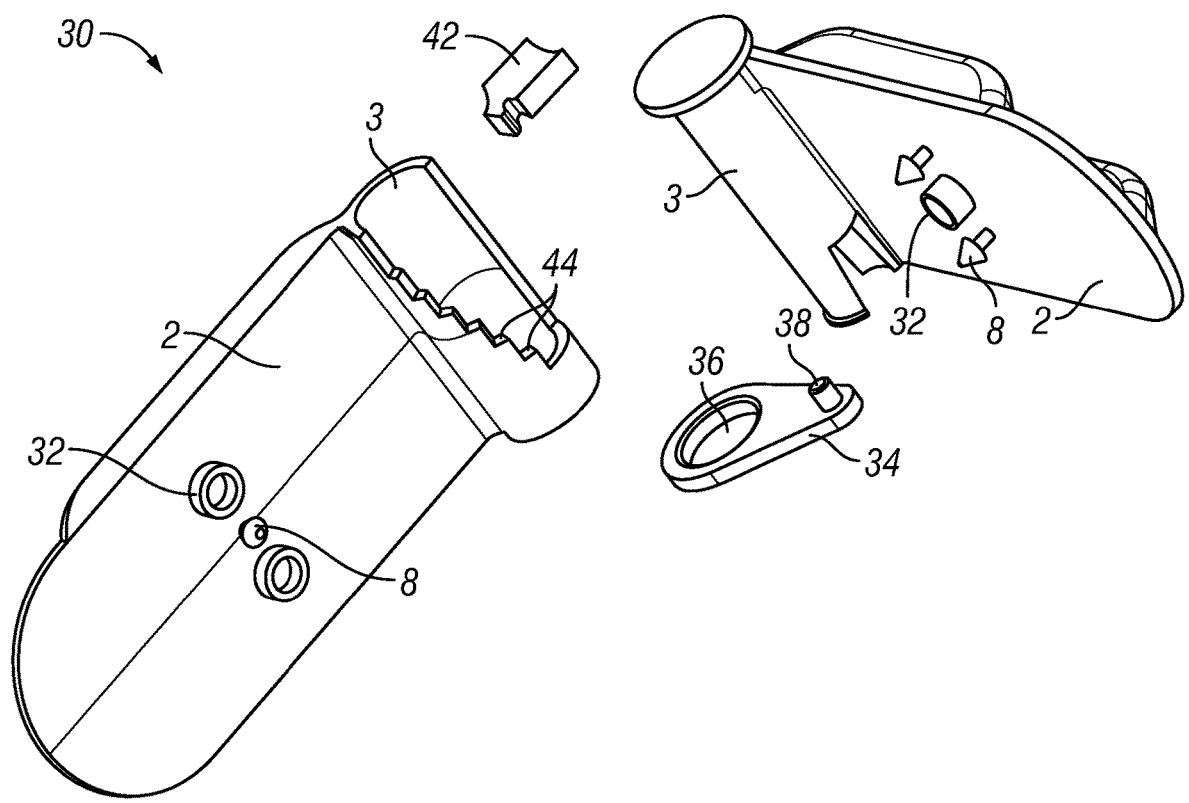
FIGS. 17A-17D show various views of a range of motion control device according to another embodiment of the present disclosure.
Figure 17B:
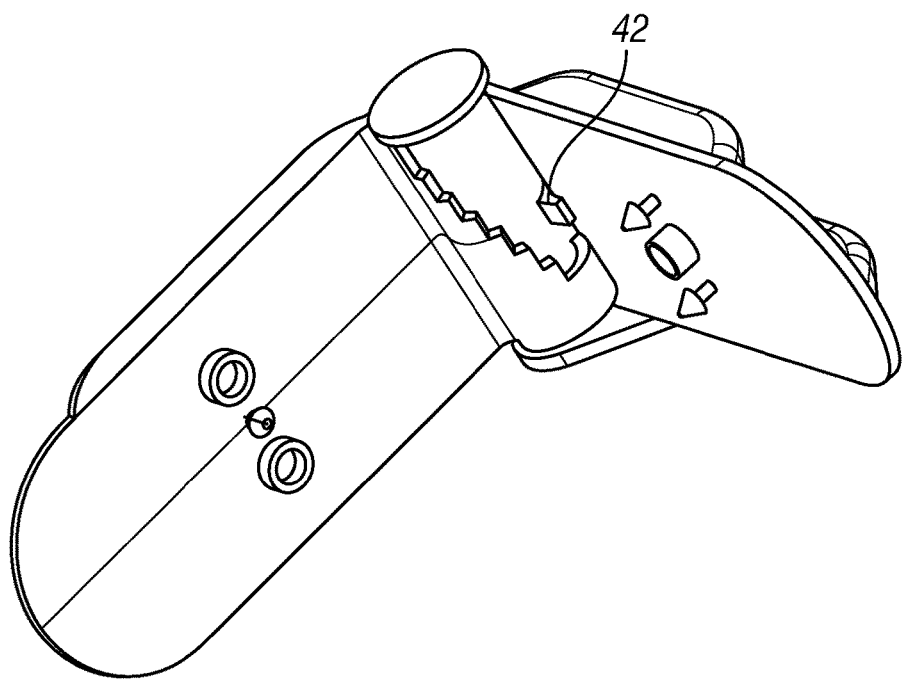
Figure 17C:
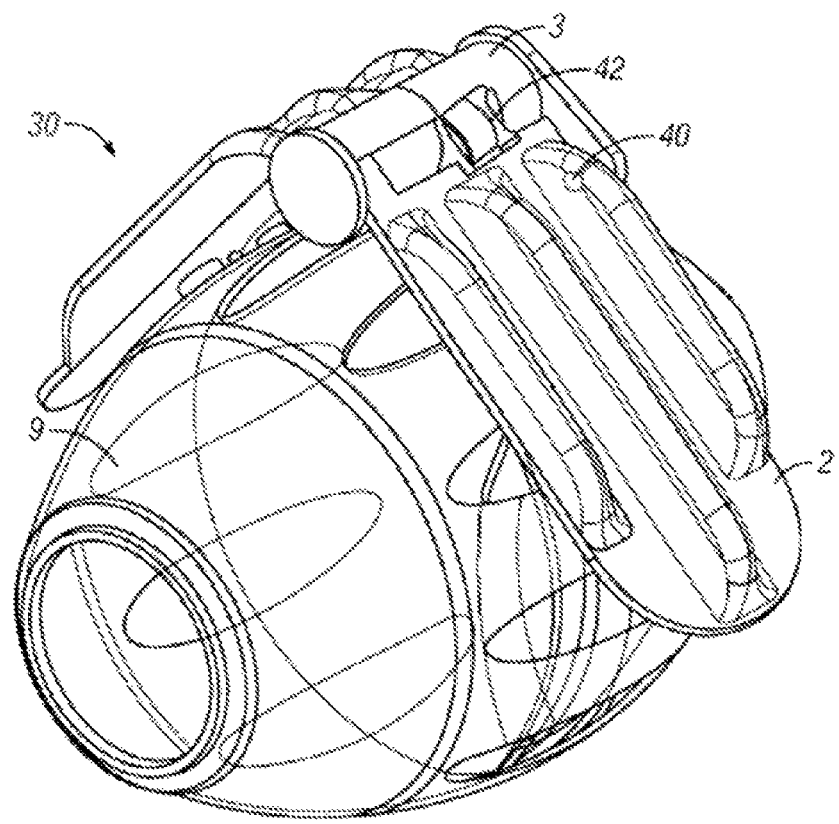
Figure 17D:
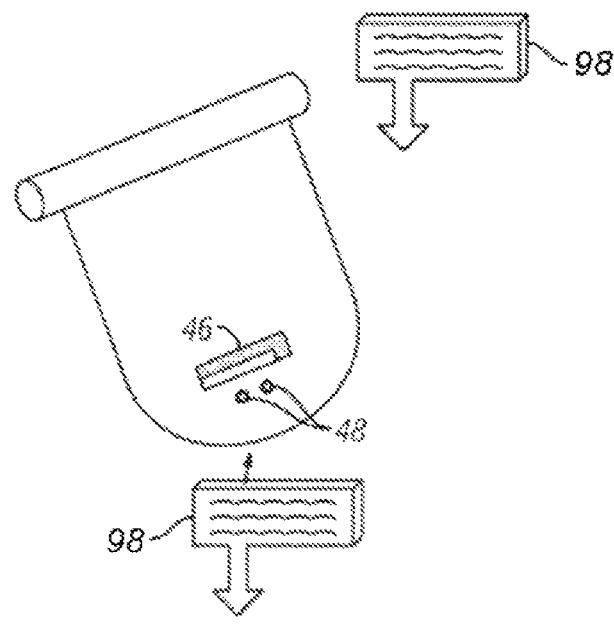
Figure 18A:
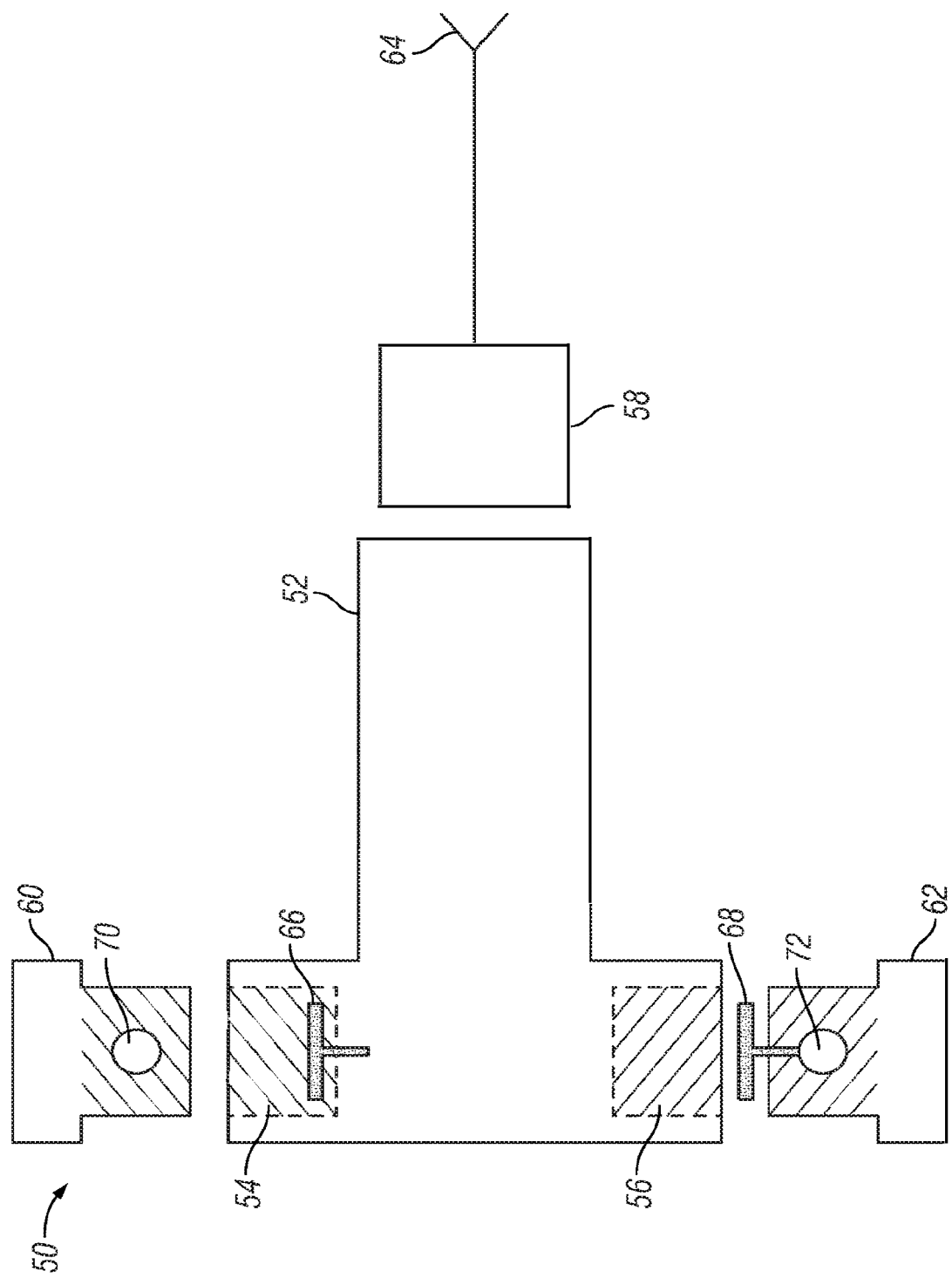
FIGS. 18A-18D illustrate various views of a pneumatic device connectable to a range of motion control device according to another embodiment of the present disclosure.
Figure 18B:
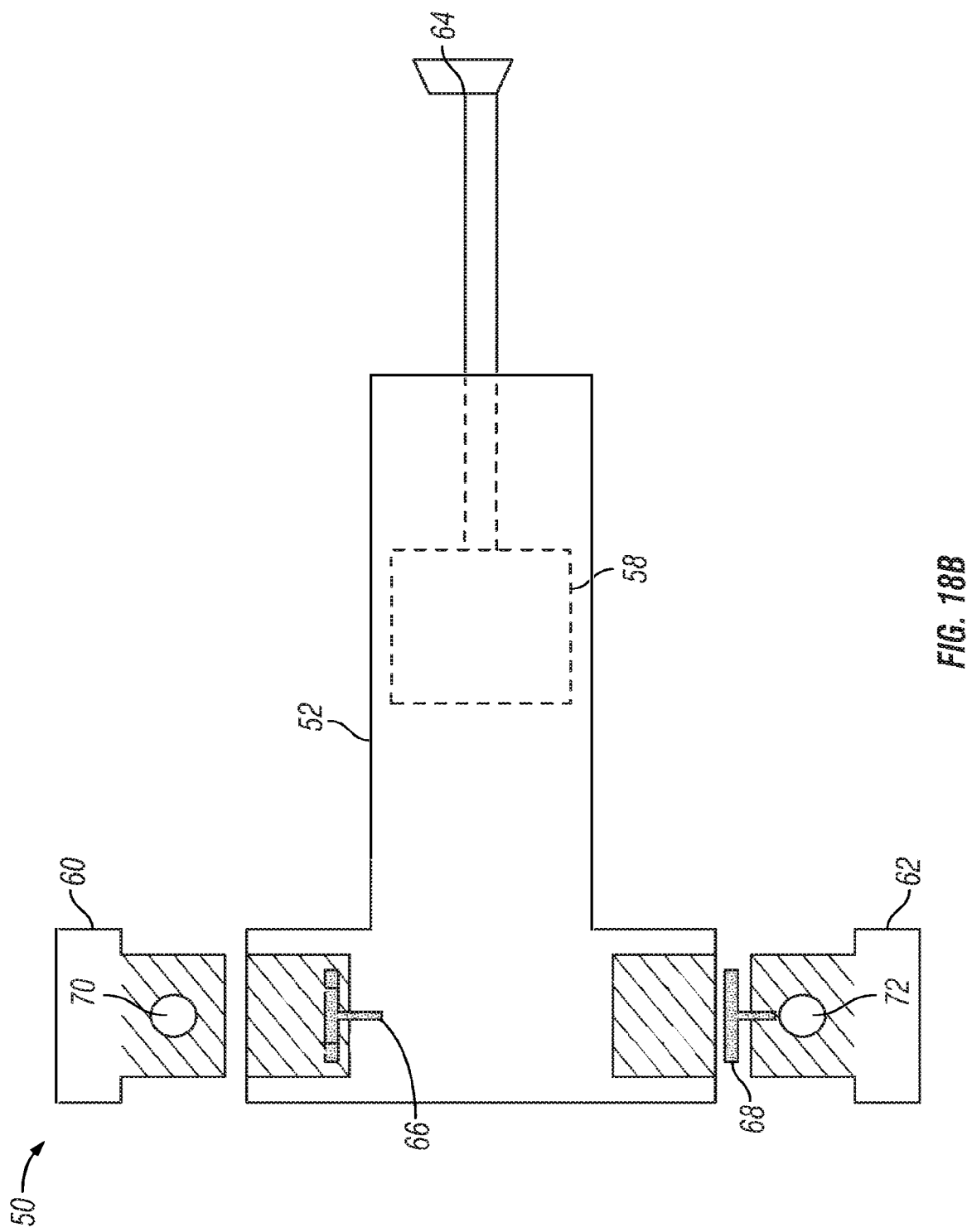
Figure 18D:
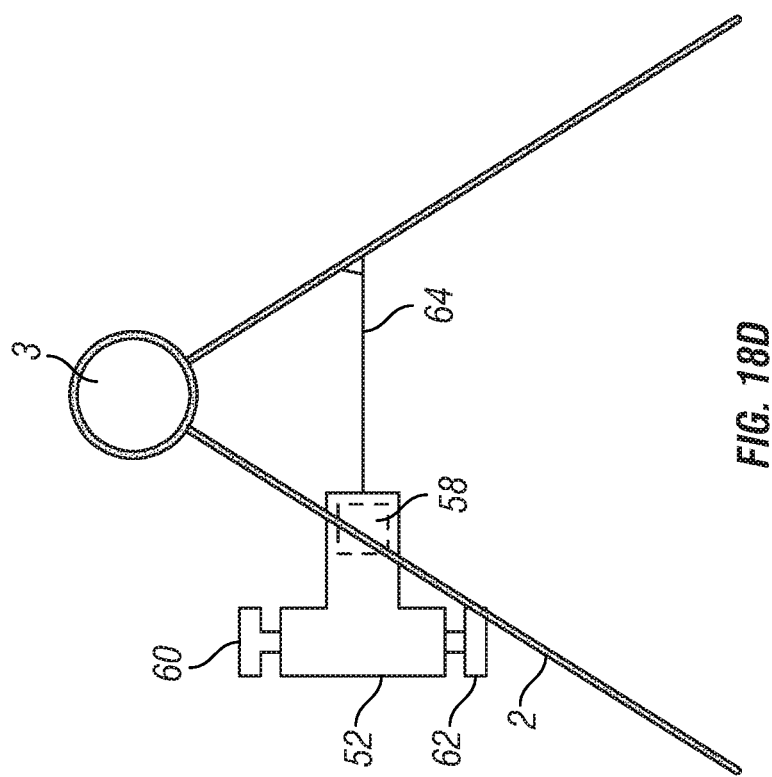
Figure 18C:
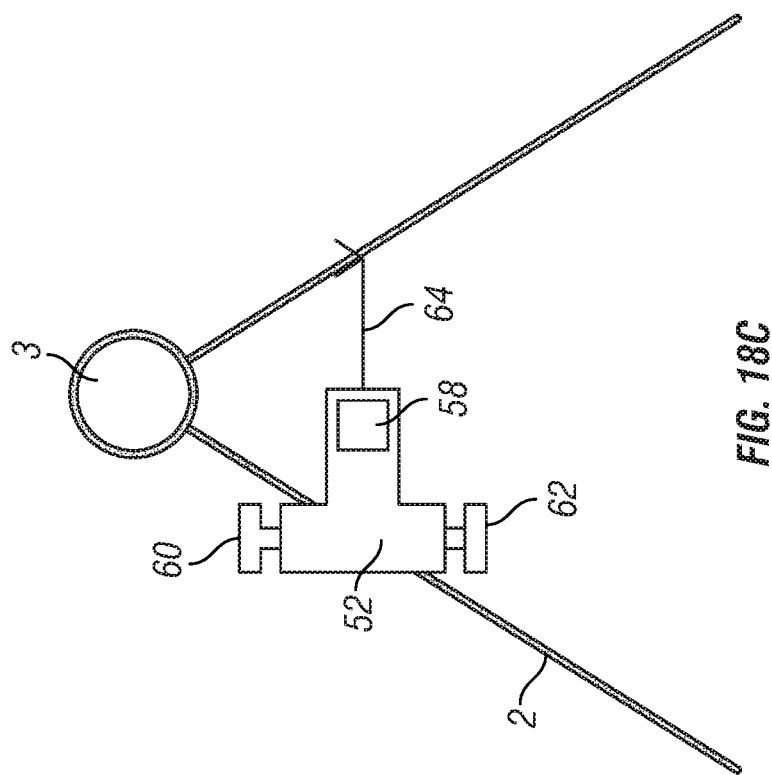
Figure 19A:
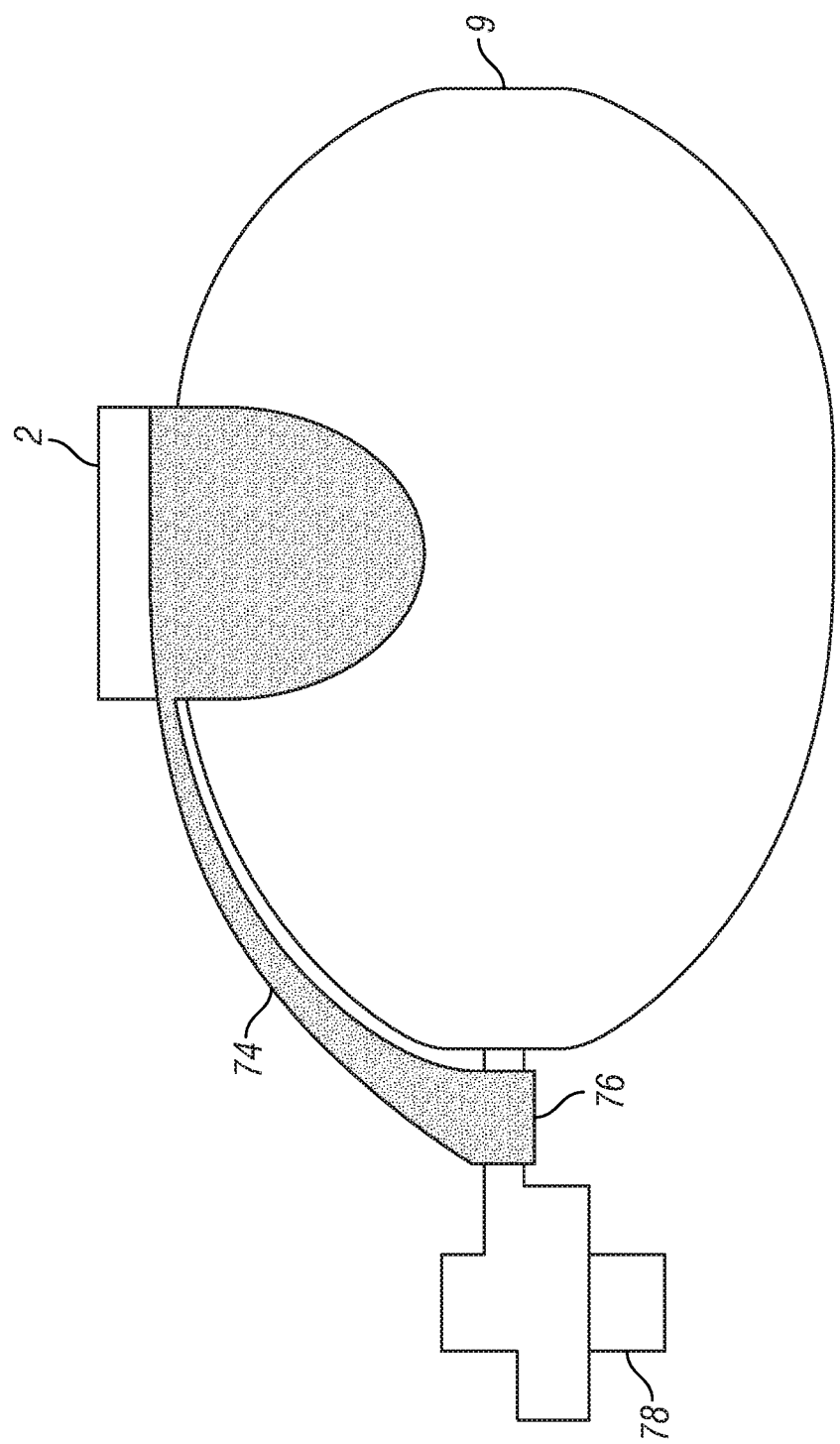
FIGS. 19A-19D illustrate a leveraging device connectable to a range of motion control device according to another embodiment of the present disclosure.
Figure 19C:
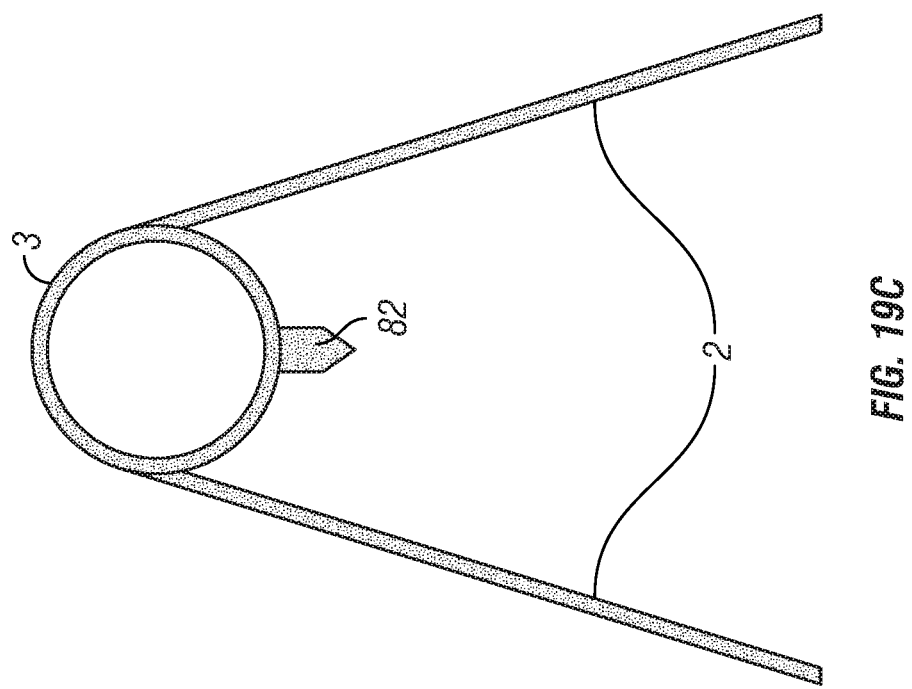
Figure 19B:
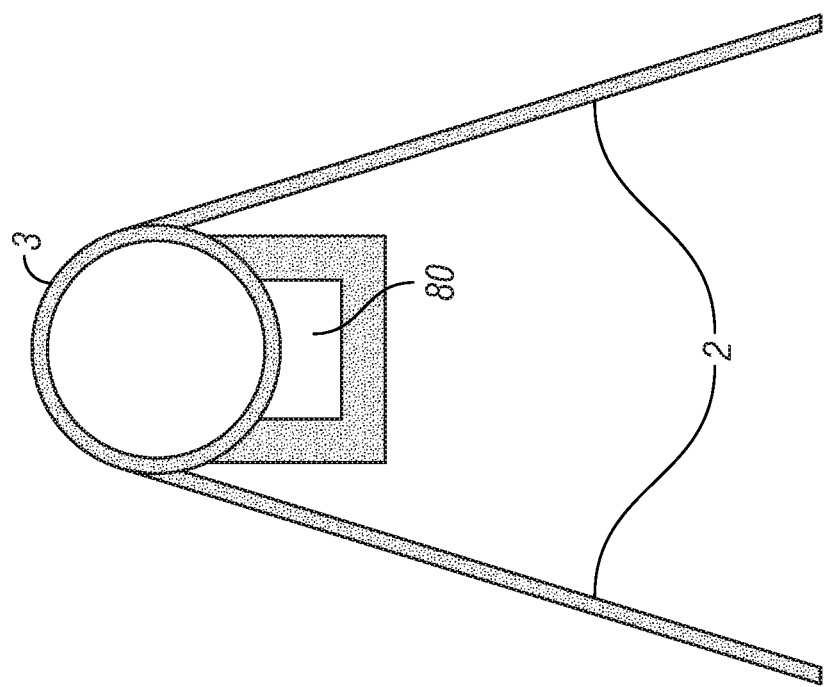
Figure 19D:
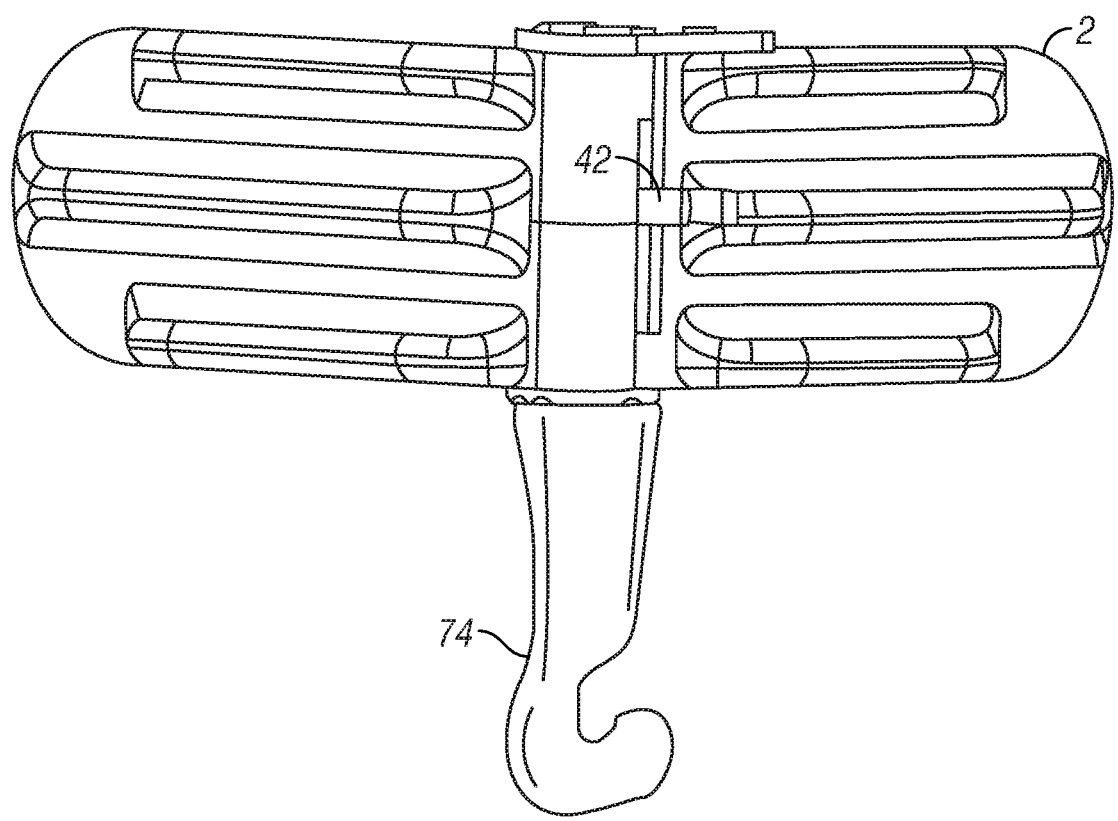

FIG. 15 illustrates a stepped range of motion control device 22 according to another embodiment of the present disclosure. In the embodiment shown, the device 22 can act similarly to the wedges/protrusions described previously, such as those shown in FIGS. 6-13. In the embodiment shown, device 22 has a plurality of steps 24 that each correspond to a volume level for a particular application. For example, steps 24 may each correspond to a particular patient category (e.g., adult, pediatric, infant) and enable a tidal volume administration appropriate for that category when the BVMR 9 is compressed at that position. In the embodiment shown, steps 24 represent lower volumes as they intrude farther into the bag.

Figure 16:
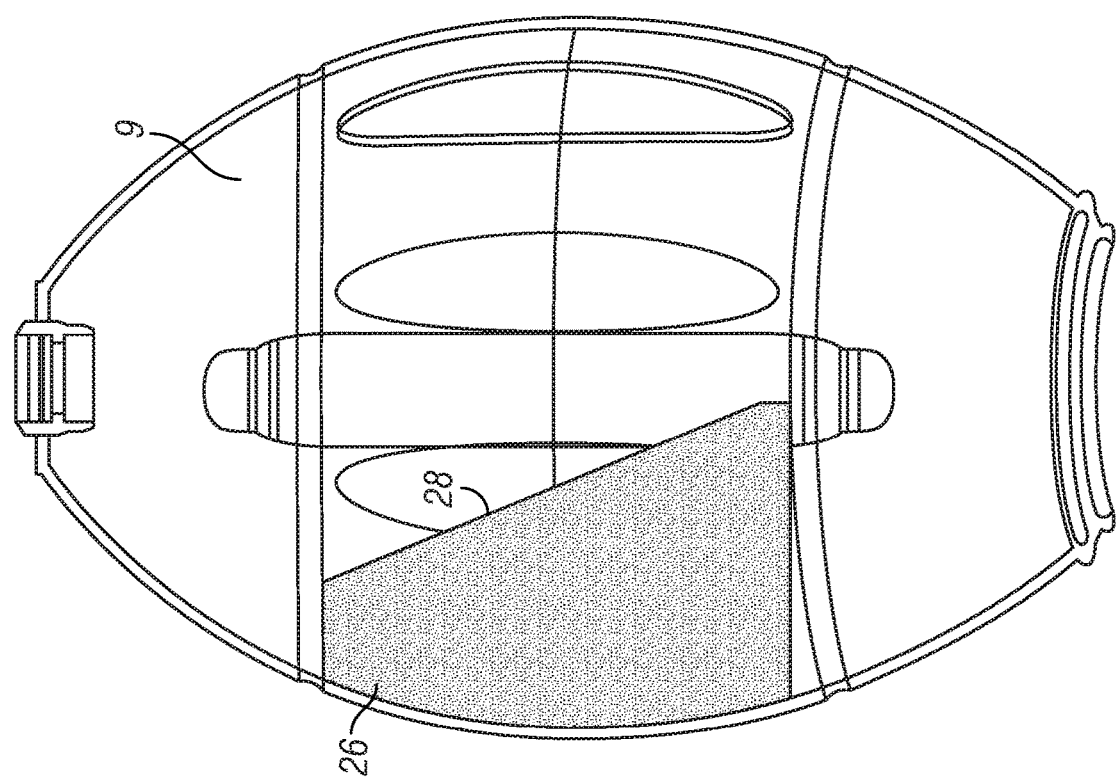
FIG. 16 illustrates a sloped range of motion control device according to another embodiment of the present disclosure.

FIG. 16 illustrates a sloped range of motion control device 26 according to another embodiment of the present disclosure. In the embodiment shown, the device 26 can act similarly to the wedges/protrusions described previously, such as those shown in FIGS. 6-13 and 15. In the embodiment shown, device 26 has a sloped edge 28 that corresponds to a plurality of volume levels for particular applications. For example, different positions along the sloped edge 28 may correspond to a particular patient category (e.g., adult, pediatric, infant) and enable a tidal volume administration appropriate for that category when the BVMR 9 is compressed at that position. In the embodiment shown, sloped edge 28 represents lower volumes as it intrudes farther into the bag.

FIGS. 17A-17D show various views of a range of motion control device 30 according to another embodiment of the present disclosure. In the embodiment shown, device 30 has two wings 2, a main body 3 (e.g., having a male component on one wing and a female component on another wing), and at least one fastener disposed on each wing 2 (e.g., barbs 8 that can penetrate a BVMR and/or snaps 32 that can snap into the BVMR). In the embodiment shown, the device 30 can be held together by a coupler 34 that has a hole 36 that can couple together the components of the main body 3 and a peg or pin 38 that can snap into a hole, orifice, or channel 40 disposed into body 3 to lock/stabilize body 3 in a desired position. In the embodiment shown, device 30 has a slider 42 that can navigate steps 44 disposed into the main body 3. Similar to FIG. 15, each step 44 can correspond to a particular volume level. A user can slide slider 42 to a step 44 corresponding to the tidal volume administration appropriate for a certain application. Peg 38 can engage with different holes/orifices 40 or slide within a channel disposed into wing 2 to accommodate various positions of device 30 depending upon the position of slider 42. In the embodiment shown in FIG. 17D, a barb 8 can be a removable barb 98 that can be inserted into a slot 46 disposed in a wing 2 and locked into position by one or more placement holders 48 (e.g., bumps, stops).

FIGS. 18A-18D illustrate various views of a pneumatic device 50 connectable to a range of motion control device according to another embodiment of the present disclosure. In the embodiment shown, pneumatic device 50 comprises a main housing 52 having an outlet opening 54 and an inlet opening 56, a plunger 58, an outlet control member 60, and an inlet control member 62. The pneumatic device 50 can be formed, or otherwise connected onto a front or rear aspect of the wings 2, or it may be formed as part of the wing members. The pneumatic device 50 may also be formed as part of a main body of the wing 2 so that housing 52 and/or plunger 58 may pass through the thickness of the wing 2, with the plunger 58 attaching to or being controlled by the underside of the opposing wing 2. In the embodiment shown, plunger 58 has one or more connective members 64 that can connect to one or more of the wings 2 described in the previous embodiments. In some embodiments, pneumatic device 50 can attach to the wings, be formed as part of the wings, or pass through the wings. In the embodiment shown, plunger 58 can move longitudinally back and forth within housing 52 based on a compression or decompression movement of wings 2. When the wings 2 are compressed together, the plunger 58 travels within housing 52 toward outlet opening 54 and inlet opening 56 and releases outlet valve 66 to let air out of outlet opening 54. In some embodiments, the outlet valve 66 can fit a corresponding hole constructed as part of the outlet control member 60. When the wings 2 are expanded, the plunger 58 travels within housing 52 away from outlet opening 54 and inlet opening 56 and releases inlet valve 68 to let air into of inlet opening 56. In some embodiments, the inlet valve 68 can fit a corresponding hole constructed as part of the inlet control member 62. In the embodiment shown, outlet opening 54 and inlet opening 56 can be reduced or enlarged by the user by moving outlet control member 60 and inlet control member 62 into and out of outlet opening 54 and inlet opening 56, respectively. In the embodiment shown, outlet control member 60 and inlet control member 62 can be moved back and forth by screwing them into or out of the respective outlet opening 54 and inlet opening 56. Outlet control member 60 has a master outlet control orifice 70 disposed within its body and inlet control member 62 has a master inlet control orifice 72 disposed within its body. Master outlet control orifice 70 and master inlet control orifice 72 can be increasingly or decreasingly exposed depending on the position of the outlet control member 60 within outlet opening 54 and inlet control member 62 within inlet opening 56, respectively. This can allow more or less air to pass through master outlet control orifice 70 and master inlet control orifice 72 and can slow down the action of the bag to allow for increased control of the rate of ejection of the volume inside the reservoir of the BVMR and/or slow down the action of the bag to allow for control of the rate of re-inflation of the BVMR.

For example, rescue breaths are supposed to be delivered over 1 second to simulate normal respiration. During ejection, inlet valve 68 will close, outlet valve 66 will open, and the air within the bag will be forced to the outlet opening 54. During re-inflation of the BVMR, the plunger 58 is pulled with the wing 2 by the inflation of the BVMR. This can cause inlet value 68 to open and outlet valve 66 to close or be "sucked closed" by the incoming airflow. For example in resuscitation only 10 breaths per minute are recommended presently, so a 5 second re-inflation period can be controlled (coupled with a 1 second ejection rate this would equal 6 seconds per cycle, and result in 10 breaths per minute). During other respiratory emergencies or general care, appropriate rates of respiration can be configured by reducing or enlarging master outlet control orifice 70 and master inlet control orifice 72 by the user. This may allow the user complete control of both the rate of ejection of the volume of the reservoir (this is a protective design to avoid barotrauma and or volu-trauma) and the rate of use of the BVMR to result in a correct rate of ventilation. Once a patient-appropriate volume is determined, the rate of ventilation can be set by the user by reducing or enlarging the master inlet control orifice 72 to the desired rate of re-inflation. The rate of ejection can then be set to meet the now established volume metric need of the patient by reducing or enlarging the master outlet control orifice 70.

FIGS. 19A-19D illustrate a leveraging device 74 connectable to a range of motion control device according to another embodiment of the present disclosure. In some embodiments, leveraging device 74 can attach to the wings 2, be formed as part of the wings, or pass through the wings 2. In some embodiments, one end of the leveraging device 74 can be made to fit around a neck 76 of an outlet 78 of the BVMR 9. In some embodiments, leveraging device 74 may be a single piece or multiple pieces and can be configured to articulate or telescope. In the embodiments shown, the end of leveraging device 74 opposite the end that fastens to neck 76 can fasten into one or more connective members of main body 3 to removably or permanently receive leveraging device 74. The connective member of main body 3 can be a recipient channel or groove 80 configured to receive the leveraging device 74 or can be at least one snapping member 82. In the embodiment shown, snapping member 82 is a male member configured to snap into a female receptacle or hole disposed into leveraging device 74. In an alternative embodiment, snapping member 82 can be a female receptacle configured to receive a male member disposed onto leveraging device 74.

Figure 20B:
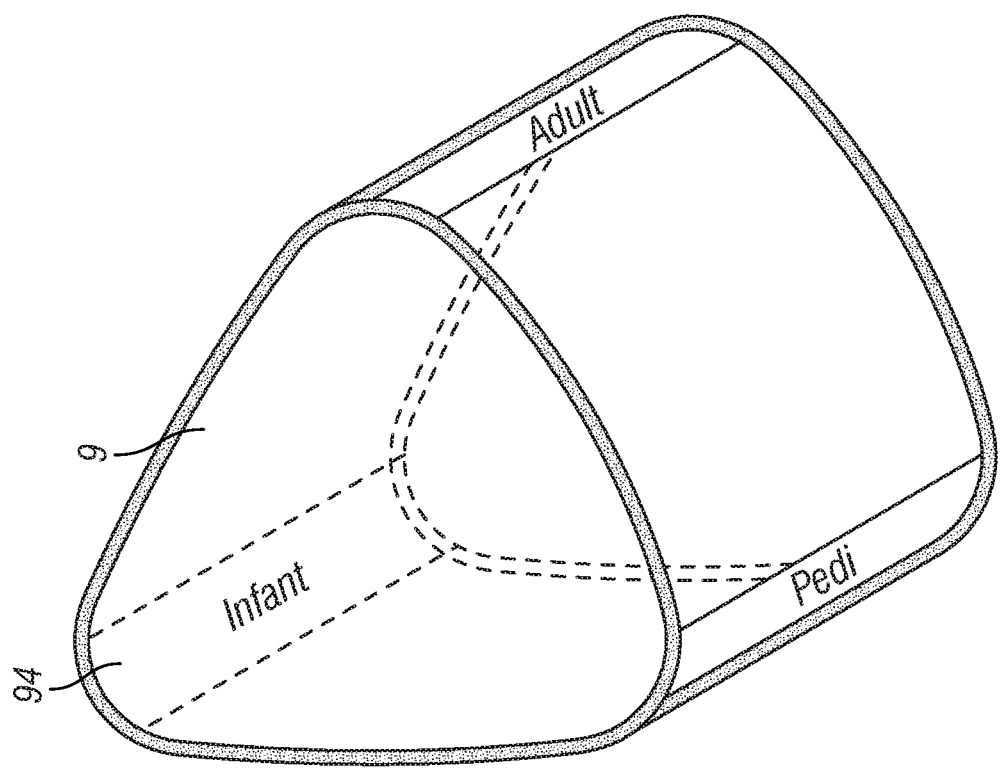
FIGS. 20A and 20B show various views of a range of motion control device according to another embodiment of the present disclosure.
Figure 20A:
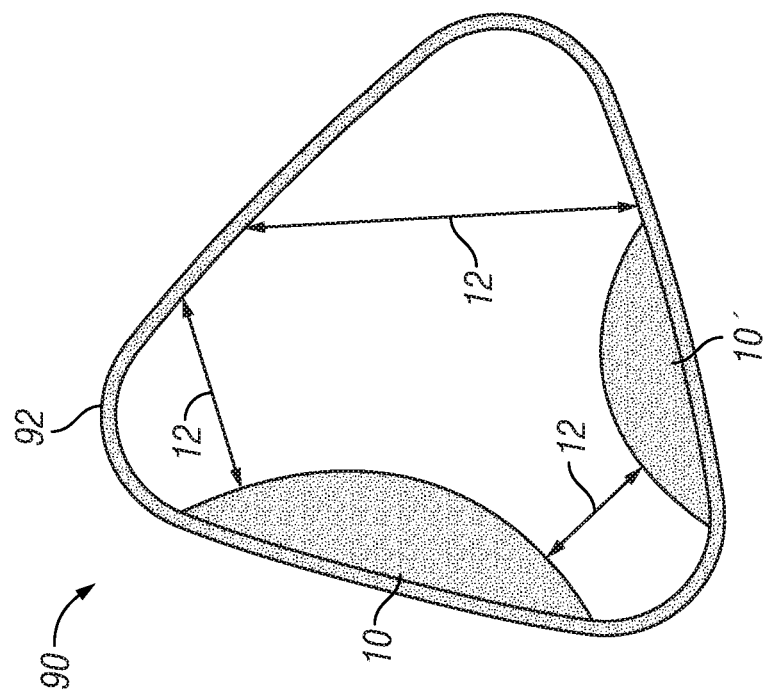

FIGS. 20A and 20B show various views of a range of motion control device 90 according to another embodiment of the present disclosure. In some embodiments, device 90 can include a BVMR 9 having multiple "corners" 92 with one or more specifically spaced wedges 10, 10' disposed between one or more of the corners 92. In the embodiment shown, there are three corners 92 that form a triangular shape. In some embodiments, there may be four corners 92 that may form a square or trapezoid shape or additional corners that form additional shapes (e.g., five corners forming a pentagon, etc.). In these embodiments, a user can apply a particular volume of air by grasping two of the corners 92 or wedges 10, 10' corresponding to a desired volume (e.g., adult, pediatric, infant). In the embodiment shown, device 90 may be marked with one or more labels 94 that denote corresponding hand positions for dispensing a desired air volume.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A device for controlling the volume of air delivered by a bag valve mask comprising:
   a first wing member configured to be attached to a bag of the bag valve mask, the first wing member having:
      a first end; and
      a second end; and
   a second wing member configured to be attached to the bag of the bag valve mask, the second wing member having:
      a first end rotatably coupled via a hinge to the first end of the first wing member; and
      a second end;
   wherein the hinge is operable in:
      a first state in which the hinge limits the first wing member to a first range of motion relative to the second wing member from an open position to a first closed position, wherein the first range of motion corresponds to a first volume of air to be delivered by the bag valve mask when the bag of the bag valve mask is disposed between the first and second wing members; and
      a second state in which the hinge limits the first wing member to a second range of motion relative to the second wing member from the open position to a second closed position, wherein the second range of motion corresponds to a second volume of air to be delivered by the bag valve mask when the bag of the bag valve mask is disposed between the first and second wing members that is greater than the first volume of air.

2. The device of claim 1, wherein the first and second wing members are curved to correspond to a curvature of the bag.

3. The device of claim 1, further comprising one or more barbs protruding from the first and second wing members for fastening the members to the bag.

4. The device of claim 1, wherein the hinge comprises a first portion defined by the first end of the first wing member, and a second portion defined by the first end of the second wing member.

5. The device of claim 1, wherein the hinge comprises a volume selector for selecting the volume of air to be delivered by the bag valve mask.

6. The device of claim 5, wherein the hinge comprises a pin received through the first wing member and into a channel defined by the second wing member for selecting the volume of air to be delivered by the bag valve mask.

7. The device of claim 1, wherein the first and second wing members comprise a point of articulation between the first and second ends of the first and second wing members.

8. A bag valve mask for delivering an adjustable amount of air to a patient, comprising:
   a mask configured to make sealing contact with the nose and mouth of the patient;
   a flexible air bag;
   a connection hose connecting the mask and the air bag, wherein when the air bag is compressed, the air contained in the air bag is supplied to the patient through the connection hose and the mask; and
   a device for limiting the amount of compression of the flexible air bag to control the volume of air delivered to a patient, wherein the device for limiting the amount of compression of the flexible air bag is coupled to the flexible air bag and comprises:

a first wing member configured to be attached to a bag of the bag valve mask, the first wing member having:
  a first end; and
  a second end; and
a second wing member configured to be attached to the bag of the bag valve mask, the second wing member having:
  a first end rotatably coupled via a hinge to the first end of the first wing member; and
  a second end;
wherein the hinge is operable in:
  a first state in which the hinge limits the first wing member to a first range of motion relative to the second wing member from an open position to a first closed position, wherein the first range of motion corresponds to a first volume of air to be delivered by the flexible air bag; and
  a second state in which the hinge limits the first wing member to a second range of motion relative to the second wing member from the open position to a second closed position, wherein the second range of motion corresponds to a second volume of air to be delivered by the flexible air bag that is greater than the first volume of air, and
wherein the flexible air bag is disposed between the first wing member and the second wing member.

9. The bag valve mask of claim 8, wherein the range of motion control mechanism comprises:
  at least one protrusion in an interior of the flexible air bag.

10. The bag valve mask of claim 8, wherein the range of motion control mechanism comprises:
  an insert configured to fit into the interior of the flexible air bag.

11. A device for controlling the volume of air delivered by a bag valve mask comprising:
  a first wing member configured to be attached to a bag of the bag valve mask, the first wing member having:
    a first end; and
    a second end;
  a second wing member configured to be attached to the bag of the bag valve mask, the second wing member having:
    a first end rotatably coupled via a hinge to the first end of the first wing member; and
    a second end,
  wherein the hinge defines a volume selector for controlling the volume of air delivered by the bag valve mask when the bag of the bag valve mask is disposed between the first and second wing members.

* * * * *

UNITED STATES PATENT AND TRADEMARK OFFICE
CERTIFICATE OF CORRECTION

PATENT NO. : 11,590,304 B2
APPLICATION NO. : 16/325869
DATED : February 28, 2023
INVENTOR(S) : Navarijo Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 491 days.

Signed and Sealed this
Seventh Day of January, 2025

Derrick Brent
*Acting Director of the United States Patent and Trademark Office*